(12) United States Patent
Bachelet et al.

(10) Patent No.: US 9,006,212 B2
(45) Date of Patent: Apr. 14, 2015

(54) COMPOSITIONS AND METHODS FOR PEST CONTROL

(75) Inventors: Ido Bachelet, Brookline, MA (US); Ram Sasisekharan, Bedford, MA (US); Mark Bulmer, Towson, MD (US); Rebeca B. Rosengaus, Boston, MA (US)

(73) Assignees: Massachusetts Institute of Technology, Cambridge, MA (US); Northeastern University, Boston, MA (US)

( * ) Notice: Subject to any disclaimer, the term of this patent is extended or adjusted under 35 U.S.C. 154(b) by 909 days.

(21) Appl. No.: 12/778,077

(22) Filed: May 11, 2010

(65) Prior Publication Data

US 2010/0317614 A1 Dec. 16, 2010

Related U.S. Application Data

(60) Provisional application No. 61/215,883, filed on May 11, 2009.

(51) Int. Cl.
*A01N 43/16* (2006.01)
*C08B 37/00* (2006.01)
*C12Q 1/34* (2006.01)

(52) U.S. Cl.
CPC *C12Q 1/34* (2013.01); *A01N 43/16* (2013.01); *C08B 37/0024* (2013.01); *G01N 2333/43552* (2013.01); *G01N 2333/43582* (2013.01); *G01N 2333/924* (2013.01)

(58) Field of Classification Search
CPC ..... A01N 43/16; A01N 25/34; C08B 37/0024
USPC .......................................................... 514/54
See application file for complete search history.

(56) References Cited

U.S. PATENT DOCUMENTS

| | | | |
|---|---|---|---|
| 3,153,613 A | 10/1964 | Moss et al. | |
| 5,908,785 A | 6/1999 | Washburn et al. | |
| 2008/0107619 A1* | 5/2008 | Scharf et al. | 424/84 |
| 2009/0221443 A1* | 9/2009 | Heller et al. | 506/16 |

FOREIGN PATENT DOCUMENTS

WO WO 2007122264 A2 * 11/2007

OTHER PUBLICATIONS

Bulmer et al. ,Biological Sciences—Applied Biological Sciences: Targeting an antimicrobial effector function in insect immunity as a pest control strategy PNAS 2009 ; pp. 1-6.*

Bulmer et al., Targeting an antimicrobial effector function in insect immunity as a pest control strategy. Proc Natl Acad Sci U S A. Aug. 4, 2009;106(31):12652-7. Epub Jun. 8, 2009.

Vargas-Arispuro et al., Lignans from Larrea tridentate (Creosote bush) as Fungal 1,3-β-glucanase inhibitors. 2009. Pesticide Biochemistry and Physiology, 94:60-63.

Warr et al., The Gram-negative bacteria-binding protein gene family: its role in the innate immune system of *Anopheles gambiae* and in anti-Plasmodium defence. Insect Mol Biol. Feb. 2008;17(1):39-51.

Bachman et al., Molecular cloning of the first metazoan beta-1,3 glucanase from eggs of the sea urchin *Strongylocentrotus purpuratus*. Proc Natl Acad Sci U S A. Jun. 25, 1996;93(13):6808-13.

Bulmer et al., Targeting an antimicrobial effector function in insect immunity as a pest control strategy. Proc Natl Acad Sci U S A. Aug. 4, 2009;106(31):12652-7. doi: 10.1073/pnas.0904063106. Epub Jun. 8, 2009.

Cremer et al., Social immunity. Curr Biol. Aug. 21, 2007;17(16):R693-702.

Genta et al., Action pattern, specificity, lytic activities, and physiological role of five digestive beta-glucanases isolated from *Periplaneta americana*. Insect Biochem Mol Biol. Nov. 2003;33(11):1085-97.

Kovalchuk et al., Purification, cDNA cloning and homology modeling of endo-1,3-beta-D-glucanase from scallop *Mizuhopecten yessoensis*. Comp Biochem Physiol B Biochem Mol Biol. Apr. 2006;143(4):473-85. Epub Feb. 10, 2006.

Leubner-Metzger et al., Functions and regulation of plant beta-1, 3-glucanases (PR-2). In: Pathogenesis-related proteins in plants. Datta (Eds.). CRC Press LLC. 1999:49-76.

Vey et al., Effects of the peptide mycotoxin destruxin E on insect haemocytes and on dynamics and efficiency of the multicellular immune reaction. J Invertebr Pathol. Jul. 2002;80(3):177-87.

Wang et al., A collagenous protective coat enables *Metarhizium anisopliae* to evade insect immune responses. Proc Natl Acad Sci U S A. Apr. 25, 2006;103(17):6647-52. Epub Apr. 13, 2006.

Zhu et al., Screening method for inhibitors against formosan subterranean termite beta-glucosidases in vivo. J Econ Entomol. Feb. 2005;98(1):41-6.

* cited by examiner

*Primary Examiner* — Janet Epps-Smith
*Assistant Examiner* — Courtney Brown
(74) *Attorney, Agent, or Firm* — Wolf, Greenfield & Sacks, P.C.

(57) ABSTRACT

Provided herein are compositions and kits comprising carbohydrate-based inhibitors that bind GNBP and/or inhibit β(1,3)-glucanase activity. Also provided are methods of using such inhibitors to protect against or treat pest infestation, as are compositions and kits comprising subparts of the carbohydrate-based inhibitors.

35 Claims, 16 Drawing Sheets

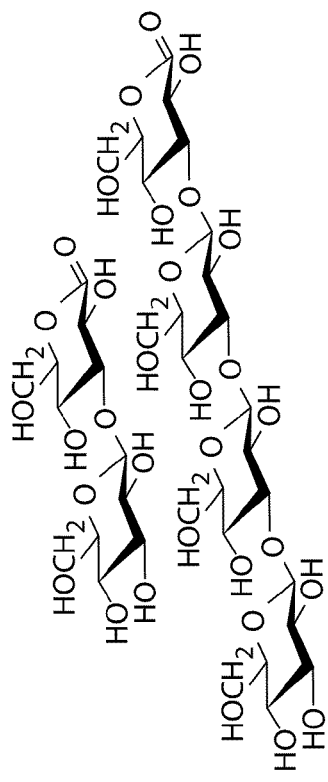
Candidate molecules for an insect GNBP inhibitor

1. Di/Tri/Tetrameric β(1,3)-D-glucan derivatives

Example: D-Glc-β(1,3)-D-glucono-Δ-lactone,
D-Glc-β(1,3)-D-Glc-β(1,3)-D-Glc-β(1,3)-D-glucono-Δ-lactone The glucose molecules may be chemically modified with group substitutions, using L instead of D isomers etc.

2. β(1,3)-D-glucan-LPS analog conjugates

Example: eritoran-[acyl spacer]-D-glucono-Δ-lactone

The two molecules may be linked by other methods for example heterobifunctional cross-linkers. Alternatively, an acyl side chain of eritoran may be employed as a spacer.

3. Polyvalent D-glucono-Δ-lactone and LPS analog conjugates

Example: GDL, Eritoran or a combination of both attached to a nanoparticle, dendrimer or polyacrylamide

Fig. 8

COMPOSITIONS AND METHODS FOR PEST CONTROL

RELATED APPLICATIONS

This application claims the benefit under 35 U.S.C. §119 of U.S. provisional application 61/215,883, filed May 11, 2009, the contents of which are incorporated herein by reference in their entirety.

GOVERNMENT SUPPORT

This invention has been made using funding from National Institutes of Health grant number 5-R01-GM057073-11 and National Science Foundation CAREER grant number DEB 0447316. The government has certain rights in the invention.

BACKGROUND OF THE INVENTION

Insect pests, such as termites, cause damage to crops and manmade structures estimated at over $30 billion per year, imposing a global challenge for human economy.

Insect immune systems are simple, efficient and still enigmatic (1-3). Somatic immunoglobulin hypervariability has been observed in *Anopheles* and *Drosophila* (4, 5) and may represent ancestral versions of adaptive immunity, although its evolutionary and functional significance in this context is not clear. Insects employ other, well-characterized mechanisms. Among these are pattern recognition receptors, which recognize molecular determinants unique to different classes of pathogenic microorganisms (1-3).

SUMMARY OF THE INVENTION

In one aspect, a method for providing protection against or treating a pest infestation is provided. In one embodiment, the method comprises contacting a pest, soil, wood, plant, seeds (e.g., stored seeds), grain (e.g., stored grain), or manmade structure with a carbohydrate-based inhibitor that binds a gram-negative bacteria binding protein (GNBP) and/or inhibits $\beta(1,3)$-glucanase activity in an amount effective to protect against or to treat the pest infestation.

In one embodiment, the carbohydrate-based inhibitor does not inhibit cellulase or stimulate feeding.

In another embodiment, the carbohydrate-based inhibitor is a di/tri/tetrameric $\beta(1,3)$-D-glucan derivative or a di/tri/tetrameric $\beta(1,3)$-L-glucan derivative. In one embodiment, the di/tri/tetrameric $\beta(1,3)$-D-glucan derivative or di/tri/tetrameric $\beta(1,3)$-L-glucan derivative is D-Glc-$\beta(1,3)$-D-glucono-$\Delta$-lactone, D-Glc-$\beta(1,3)$-D-Glc-$\beta(1,3)$-D-Glc-$\beta(1,3)$-D-glucono-$\Delta$-lactone, L-Glc-$\beta(1,3)$-L-glucono-$\Delta$-lactone, or L-Glc-$\beta(1,3)$-L-Glc-$\beta(1,3)$-L-Glc-$\beta(1,3)$-L-glucono-$\Delta$-lactone.

In a further embodiment, the carbohydrate-based inhibitor is a $\beta(1,3)$-D-glucan-lipopolysaccharide (LPS) conjugate or a $\beta(1,3)$-L-glucan-LPS conjugate. In one embodiment, the $\beta(1,3)$-D-glucan-LPS conjugate is eritoran-D-glucono-$\Delta$-lactone. In another embodiment, the $\beta(1,3)$-L-glucan-LPS conjugate is eritoran-L-glucono-$\Delta$-lactone. In yet another embodiment, the $\beta(1,3)$-D-glucan or $\beta(1,3)$-L-glucan is conjugated to the LPS with an acyl spacer. In still another embodiment, the $\beta(1,3)$-D-glucan or $\beta(1,3)$-L-glucan is conjugated to the LPS with a heterobifunctional cross-linker.

In still another embodiment, the carbohydrate-based inhibitor is a polyvalent D-glucono-D-lactone-LPS conjugate or a polyvalent L-glucono-L-lactone-LPS conjugate. In one embodiment, the polyvalent D-glucono-D-lactone-LPS conjugate or a polyvalent L-glucono-L-lactone-LPS conjugate is conjugated to a nanoparticle. In another embodiment, the polyvalent D-glucono-D-lactone-LPS conjugate or a polyvalent L-glucono-L-lactone-LPS conjugate is conjugated to a dendrimer. In yet another embodiment, the polyvalent D-glucono-D-lactone-LPS conjugate or a polyvalent L-glucono-L-lactone-LPS conjugate is conjugated to polyacrylamide. In still another embodiment, the polyvalent D-glucono-D-lactone or polyvalent L-glucono-L-lactone is D-$\delta$-gluconolactone (GDL). In a further embodiment, the LPS is eritoran.

In a further embodiment, the carbohydrate-based inhibitor is conjugated to a nanoparticle.

In yet a further embodiment, the carbohydrate-based inhibitor is conjugated to a dendrimer.

In still a further embodiment, the carbohydrate-based inhibitor is conjugated to polyacrylamide.

In another aspect, a composition comprising a carbohydrate-based inhibitor that binds a GNBP and/or inhibits $\beta(1,3)$-glucanase activity is provided. In one embodiment, the carbohydrate-based inhibitor does not inhibit cellulase and stimulate feeding. In another embodiment, the carbohydrate-based inhibitor is in an amount effective to protect against or treat a pest infestation.

In yet another embodiment, the carbohydrate-based inhibitor is a di/tri/tetrameric $\beta(1,3)$-D-glucan derivative or a di/tri/tetrameric $\beta(1,3)$-L-glucan derivative. In one embodiment, the di/tri/tetrameric $\beta(1,3)$-D-glucan derivative or di/tri/tetrameric $\beta(1,3)$-L-glucan derivative is D-Glc-$\beta(1,3)$-D-glucono-$\Delta$-lactone, D-Glc-$\beta(1,3)$-D-Glc-$\beta(1,3)$-D-Glc-$\beta(1,3)$-D-glucono-$\Delta$-lactone, L-Glc-$\beta(1,3)$-L-glucono-$\Delta$-lactone, or L-Glc-$\beta(1,3)$-L-Glc-$\beta(1,3)$-L-Glc-$\beta(1,3)$-L-glucono-$\Delta$-lactone.

In still another embodiment, the carbohydrate-based inhibitor is a $\beta(1,3)$-D-glucan-LPS conjugate or a $\beta(1,3)$-D-glucan-LPS conjugate. In one embodiment, the $\beta(1,3)$-D-glucan-LPS conjugate is eritoran-D-glucono-$\Delta$-lactone. In another embodiment, the $\beta(1,3)$-L-glucan-LPS conjugate is eritoran-L-glucono-$\Delta$-lactone. In still another embodiment, the $\beta(1,3)$-D-glucan or $\beta(1,3)$-L-glucan is conjugated to the LPS with an acyl spacer. In yet another embodiment, the $\beta(1,3)$-D-glucan or $\beta(1,3)$-L-glucan is conjugated to the LPS with a heterobifunctional cross-linker.

In a further embodiment, the carbohydrate-based inhibitor is a polyvalent D-glucono-D-lactone-LPS conjugate or a polyvalent L-glucono-L-lactone-LPS conjugate. In one embodiment, the polyvalent D-glucono-D-lactone-LPS conjugate or a polyvalent L-glucono-L-lactone-LPS conjugate is conjugated to a nanoparticle. In another embodiment, the polyvalent D-glucono-D-lactone-LPS conjugate or a polyvalent L-glucono-L-lactone-LPS conjugate is conjugated to a dendrimer. In still another embodiment, the polyvalent D-glucono-D-lactone-LPS conjugate or a polyvalent L-glucono-L-lactone-LPS conjugate is conjugated to polyacrylamide. In yet another embodiment, the polyvalent D-glucono-D-lactone or polyvalent L-glucono-L-lactone is GDL. In one embodiment, the LPS is eritoran.

In still a further embodiment, the carbohydrate-based inhibitor is conjugated to a nanoparticle.

In yet a further embodiment, the carbohydrate-based inhibitor is conjugated to a dendrimer.

In another embodiment, the carbohydrate-based inhibitor is conjugated to polyacrylamide.

In one embodiment of any of the methods or compositions provided herein, the carbohydrate-based inhibitor does not inhibit $\alpha$-1,4-glucosidase. In another embodiment of any of the methods or compositions provided herein, the carbohydrate-based inhibitor does not inhibit $\beta$-1,4-glucosidase. In yet another embodiment of any of the methods or compositions provided herein, the carbohydrate-based inhibitor does not inhibit either α-1,4-glucosidase or β-1,4-glucosidase. In still another embodiment of any of the methods or compositions provided herein, the carbohydrate-based inhibitor only inhibits β(1,3)-glucanase activity. In another embodiment of any of the methods or compositions provided herein, the carbohydrate-based inhibitor inhibits β(1,3)-glucanase activity and does not inhibit any other glucanase and/or glucosidase enzymatic activity.

In another embodiment of any of the methods or compositions provided herein, the carbohydrate-based inhibitor is not gluconolactone and/or does not comprise gluconolactone or a derivative thereof.

In another embodiment of any of the methods or compositions provided herein, the β(1,3)-glucanase activity is the β(1,3)-glucanase activity of a GNBP. In one embodiment, the GNBP is insect GNBP. In another embodiment, the insect GNBP is termite GNBP. In one embodiment, the GNBP is GNBP-1 or GNBP-2. In another embodiment, the GNBP is termite GNBP-2. In certain embodiments, the termite GNBP-2 has a sequence as set forth in GeneBank accession Nos: GU906856-GU906821. In other embodiments, the GNBP has a sequence as set forth in any of the sequences provided herein.

In another embodiment of any of the methods or compositions provided herein, the carbohydrate-based inhibitor binds a GNBP and/or inhibits β(1,3)-glucanase activity of an insect, such as a termite, a fly, a moth, an ant, a beetle, a mosquito, a silk worm with a GNBP that is at least 50%, 60%, 70%, 80%, 90%, 95%, 96%, 97%, 98%, or 99% homologous to tGNBP-2. In certain embodiments, the docking site may comprise one or more positions I-VI equivalent to residue positions (in *N. graveolus* sequence): I 56, II 143, III 146, IV 172, V 179, VI 308, wherein position I is an acidic residue (E/D), II is a basic residue (R/H), III is an acidic residue (E/D), IV is a hydrophobic residue (W, M, L), V is any residue, and VI is tryptophan (Y).

In still another embodiment of any of the methods or compositions provided herein, the pest infestation is insect infestation. In one embodiment, the insect infestation is termite infestation. In another embodiment, the termites of the termite infestation are of the *N. corniger, Z. augusticollis, C. secundus, R. virginicus* or *R. flavipes* species.

In yet another embodiment of any of the methods or compositions provided herein, the contacting comprises applying or spraying the carbohydrate-based inhibitor onto the pest, soil, wood, plant, seeds (e.g., stored seeds), grain (e.g., stored grain), or manmade structure.

In a further embodiment of any of the methods or compositions provided herein, the pest, soil, wood, plant, seeds (e.g., stored seeds), grain (e.g., stored grain), or manmade structure is further contacted with another pesticide or the composition further comprises another pesticide. In some embodiments, the pesticide is an insecticide, a fungicide or a herbicide.

In still another aspect, a kit comprising a container containing any of the carbohydrate-based inhibitors provided herein is provided. In one embodiment, the kit further contains an additional container. In another embodiment, the additional container contains another pesticide.

In yet another aspect, a kit comprising a first container containing a carbohydrate-based inhibitor that binds a GNBP and/or inhibits β(1,3)-glucanase activity is provided. In one embodiment, the kit further comprises a second container. In one embodiment, the second container comprises a nanoparticle. In another embodiment, the second container comprises a dendrimer. In yet another embodiment, the second container comprises polyacrylamide.

In one embodiment of any of the kits provided herein, the carbohydrate-based inhibitor is a di/tri/tetrameric β(1,3)-D-glucan derivative or a di/tri/tetrameric β(1,3)-L-glucan derivative. In one embodiment, the di/tri/tetrameric β(1,3)-D-glucan derivative or di/tri/tetrameric β(1,3)-L-glucan derivative is D-Glc-β(1,3)-D-glucono-Δ-lactone, D-Glc-β(1,3)-D-Glc-β(1,3)-D-Glc-β(1,3)-D-glucono-Δ-lactone, L-Glc-β(1,3)-L-glucono-Δ-lactone, or L-Glc-β(1,3)-L-Glc-β(1,3)-L-Glc-β(1,3)-L-glucono-Δ-lactone. In another embodiment, the carbohydrate-based inhibitor is a β(1,3)-D-glucan-LPS conjugate or a β(1,3)-L-glucan-LPS conjugate. In yet another embodiment, the β(1,3)-D-glucan-LPS conjugate is eritoran-D-glucono-Δ-lactone. In still another embodiment, the β(1,3)-L-glucan-LPS conjugate is eritoran-L-glucono-Δ-lactone. In a further embodiment, the β(1,3)-D-glucan or β(1,3)-L-glucan is conjugated to the LPS with an acyl spacer. In yet a further embodiment, the β(1,3)-D-glucan or β(1,3)-L-glucan is conjugated to the LPS with a heterobifunctional cross-linker. In still a further embodiment, the carbohydrate-based inhibitor is a polyvalent D-glucono-D-lactone-LPS conjugate or a polyvalent L-glucono-L-lactone-LPS conjugate. In another embodiment, the polyvalent D-glucono-D-lactone or polyvalent L-glucono-L-lactone is GDL. In one embodiment, the LPS is eritoran.

In still another aspect, a kit comprising a first container containing a β(1,3)-D-glucan or β(1,3)-L-glucan is provided. In one embodiment, the kit further comprises a second container. In one embodiment, the second container comprises a LPS. In another embodiment, the β(1,3)-D-glucan or β(1,3)-L-glucan is D-glucono-Δ-lactone or L-glucono-Δ-lactone. In still another embodiment, the LPS is eritoran. In yet another embodiment, the kit further comprises a third container. In one embodiment, the third container comprises a molecule for conjugating the β(1,3)-D-glucan or β(1,3)-L-glucan to the LPS. In one embodiment, the molecule for conjugating is an acyl spacer. In another embodiment, the molecule for conjugating is a heterobifunctional cross-linker.

In yet another aspect, a kit comprising a first container containing a polyvalent D-glucono-D-lactone or polyvalent L-glucono-L-lactone is provided. In one embodiment, the kit further comprises a second container. In one embodiment, the second container comprises a LPS. In another embodiment, the polyvalent D-glucono-D-lactone or polyvalent L-glucono-L-lactone is GDL. In still another embodiment, the LPS is eritoran.

In a further aspect, a method of determining whether or not a compound protects against or treats pest infestation is provided. In one embodiment, the method comprises contacting a GNBP and determining whether or not it is bound or its β(1,3)-glucanase activity is inhibited by the compound, wherein when the compound is bound to GNBP and/or inhibits its β(1,3)-glucanase activity the compound protects against or treats pest infestation. In one embodiment, the determination is only whether or not its β(1,3)-glucanase activity is inhibited. In one embodiment, the method is carried out in vitro using an isolated and/or recombinant GNBP. In another embodiment, the method is carried out in vivo using a test insect. In certain embodiments, binding of a test compound to GNBP and/or inhibition of β(1,3)-glucanase activity by the test compound is determined by comparing the GNBP binding and/or inhibition of β(1,3)-glucanase activity by the test compound with GNBP binding and/or inhibition of β(1,3)-glucanase activity by a control compound with known binding and/or inhibition activity. In one embodiment, a control compound is known to exhibit GNBP binding and/or inhibition activity (positive control). In another embodiment, a control compound is known not to exhibit GNBP binding and/or inhibition activity (negative control).

In one embodiment of any of the methods of determining provided, the GNBP is insect GNBP. In one embodiment, insect GNBP is termite GNBP. In another embodiment, the GNBP is GNBP-1 or GNBP-2. In one embodiment, the GNBP is termite GNBP-2. In certain embodiments, the termite GNBP-2 has a sequence as set forth in GeneBank accession Nos: GU906856-GU906821. In other embodiments, the GNBP has a sequence as set forth in any of the sequences provided herein.

In yet another aspect, uses of a carbohydrate-based inhibitor that binds a GNBP and/or inhibits $\beta(1,3)$-glucanase activity are provided. In certain embodiments, carbohydrate-based inhibitors are provided for use in providing protection against or treating a pest infestation. In certain embodiments, carbohydrate-based inhibitors are provided for use in inhibiting $\beta(1,3)$-glucanase activity in an insect. In certain embodiments, carbohydrate-based inhibitors are provided for use in inhibiting $\beta(1,3)$-glucanase activity in an insect, wherein the insect is a termite, fly, moth, ant, beetle, mosquito, or silk worm. In certain embodiments, uses of a carbohydrate-based inhibitor that binds a GNBP and/or inhibits $\beta(1,3)$-glucanase activity are provided, wherein the carbohydrate-based inhibitor is conjugated to a nanoparticle, a dendrimer or a polyacrylamide. In certain embodiments, uses of a carbohydrate-based inhibitor that binds a GNBP and/or inhibits $\beta(1,3)$-glucanase activity are provided, wherein the carbohydrate-based inhibitor does not inhibit $\alpha$-1,4-glucosidase and/or $\beta$-1,4-glucosidase. In one embodiment, uses of a carbohydrate-based inhibitor are provided, wherein the carbohydrate-based inhibitor does not inhibit cellulase and stimulate feeding.

These and other aspects of the invention will be described in further detail in connection with the detailed description of the invention.

BRIEF DESCRIPTION OF THE FIGURES

FIG. 8 is a schematic of examples of the carbohydrate-based inhibitors of β(1,3)-glucanase activity provided herein.

DETAILED DESCRIPTION OF THE INVENTION

Figure 1:
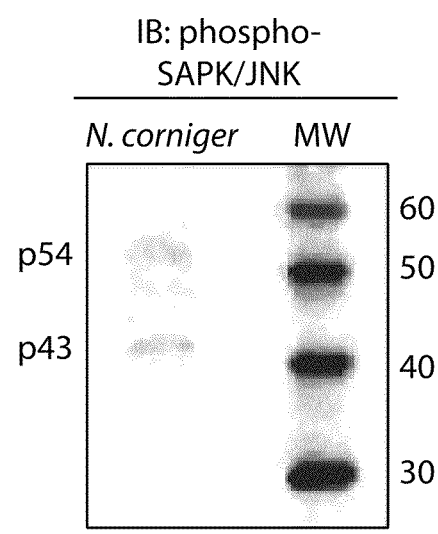
FIG. 1 shows the cross reactivity of anti phospho-SAPK/JNK to termites (antibody dilution 1:1000).

Gram-negative bacteria binding proteins (GNBPs) are a class of conserved receptors (6, 7) that signal the presence of pathogens once they enter the hemocoel (8). Insect GNBPs contain regions with significant homology to bacterial β-glucanases, especially β(1,3)- and β(1,3)(1,4)-glucanases (6, 9-11) and likely represent evolutionary descendants of enzymes originally serving homeostatic or digestive functions. Several peptidoglycan recognition proteins (PGRPs), members of a different receptor group in mammals and insects, are active amidases that either initiate protective signaling cascades or are directly bactericidal (12). GNBPs are believed to have lost enzymatic activity and are thought to serve only as pattern recognition receptors (9, 10, 13).

A strategy for compromising insect immunity that can lead to the development of nontoxic, sustainable pest control methods is presented herein. Gram-negative bacteria binding proteins (GNBPs) are critical for sensing pathogenic infection and triggering effector responses. For example, termite GNBP-2 (tGNBP-2, e.g. GeneBank accession Nos: GU906856-GU906821) shows β(1,3)-glucanase effector activity previously unknown in animal immunity, and is a pleiotropic pattern recognition receptor as well as an antimicrobial protein. Termites incorporate this protein into the nest building material, functioning as a nest-embedded sensor that cleaves and releases pathogenic components, priming termites for improved antimicrobial immunity. Presented herein are inexpensive, nontoxic small molecule glycomimetics that block, for example, tGNBP-2, exposing termites in vivo to accelerated infection and death from specific and opportunistic pathogens. Such molecules, introduced into building materials and agricultural methods, can protect valuable assets from pests. For example, while not being bound to any particular theory, termites are vulnerable to infections because their colonies survive for many years and are composed of closely related kin that share food, pheromones and symbionts through direct contact (Schmid-Hempel 1998, Princeton University Press, Princeton, N.J. 409 pp.), conditions and characteristics that favor the rapid spread of disease. Termites also compete directly with microbes in the consumption of cellulosic materials. This is especially true of subterranean termites that live and forage in soil and decaying wood. Viral and bacterial pathogens usually enter the insect through the alimentary tract, and many fungal pathogens can directly penetrate the insect cuticle (Gillespie et al. 2000, *Arch. Insect Biochem. Physiol.* 44: 49-68; Roberts and Humber 1981, Biology of conidial fungi (Cole, G T and Kendrick, B, eds.). Vol. 2, pp. 201-236. Academic Press, New York.).

It is shown herein that a termite GNBP demonstrates β(1, 3)-glucanase activity that is an effector function in antimicrobial defense. By analysis of the structure/function relationships of this protein small molecule glycomimetics that are capable of blocking it are presented, thus suppressing the insect's immune system and exposing it to attacks from specific and opportunistic pathogens (such as viral, bacterial and fungal pathogens). These molecules represent an inexpensive, nontoxic and environmentally safe alternative to toxic pesticide chemicals. Provided herein are, therefore, compositions and kits comprising carbohydrate-based inhibitors that bind a GNBP and/or inhibit β(1,3)-glucanase activity.

Carbohydrate-based inhibitor that bind GNBP and/or inhibits β(1,3)-glucanase activity include those that bind to and/or inhibit GNBP of an insect, such as termites, flies, moths, ants, beetles, mosquitoes, silk worms and other insects that is at least 50%, 60%, 70%, 80%, 90%, 95%, 96%, 97%, 98%, or 99% homologous to tGNBP-2. In certain embodiments, the docking site may comprise positions I-VI equivalent to residue positions (in *N. graveolus* sequence): I 56, II 143, III 146, IV 172, V 179, VI 308, wherein position I is an acidic residue (E/D), II is a basic residue (R/H), III is an acidic residue (E/D), IV is a hydrophobic residue (W, M, L), V is any residue, and VI is tryptophan (Y).

Also provided are methods of using such inhibitors to protect against or treat pest infestation, as are compositions and kits comprising subparts of the carbohydrate-based inhibitors.

As used herein, "carbohydrate-based" refers to a molecule that has within its structure a carbohydrate or derivative thereof. It will be appreciated by one of ordinary skill in the art that such carbohydrates in some embodiments are saccharides (e.g., monosaccharides or disaccharides). The carbohydrate-based inhibitors, in some embodiments, can be a derivative of a monosaccharide, such as an aldohexose, ketohexose, a disaccharide, or one of the aforementioned molecules with one or more carbonyl groups replacing the hydroxy groups on the carbon ring. Aldohexoses include glucose, galactose, mannose, allose, altrose, tallose, gulose, and idose. Ketohexoses include fructose, sorbose, psicose, and tagatose. Disaccharides include sucrose, lactose, maltose, cellobiose, laminaribiose, xylobiose, mannobiose, and isomaltose. The carbohydrate-based inhibitors, in some embodiments, have a β(1,3) glycosidic linkage at the reducing end.

The carbohydrate-based inhibitors also include di/tri/tetrameric β(1,3)-glucan derivatives such as di/tri/tetrameric β(1,3)-D-glucan derivatives and di/tri/tetrameric β(1,3)-L-glucan derivatives. In some embodiments, the di/tri/tetrameric β(1,3)-glucan derivative is D-Glc-β(1,3)-D-glucono-Δ-lactone, D-Glc-β(1,3)-D-Glc-β(1,3)-D-Glc-β(1,3)-D-glucono-Δ-lactone, L-Glc-β(1,3)-L-glucono-Δ-lactone, or L-Glc-β(1,3)-L-Glc-β(1,3)-L-Glc-β(1,3)-L-glucono-Δ-lactone. The carbohydrate-based inhibitors also include β(1,3)-glucan-lipopolysaccharide (LPS) conjugates such as β(1,3)-D-glucan-lipopolysaccharide (LPS) conjugates and β(1,3)-L-glucan-LPS conjugates. In one embodiment, the β(1,3)-D-glucan-LPS conjugate is eritoran-D-glucono-Δ-lactone. In another embodiment, the β(1,3)-L-glucan-LPS conjugate is eritoran-L-glucono-Δ-lactone. The carbohydrate-based inhibitors also include polyvalent D-glucono-D-lactone-LPS conjugates and polyvalent L-glucono-L-lactone-LPS conjugates. In one embodiment, the polyvalent D-glucono-D-lactone or polyvalent L-glucono-L-lactone is D-δ-gluconolactone (GDL). In another embodiment, the LPS is eritoran.

These molecules can be synthesized from different precursors. One precursor, for example, is a β(1,3)-D-glucan isolated from any of a number of abundant natural sources (e.g., seaweed, algae, baker's yeast, barley and similar sources). Such a precursor can be fragmented by partial acid hydrolysis or acetolysis and then oxidized to yield a carbonyl group in place of the reducing end, or subjected to reductive amination to ammonium acetate and sodium borohydride to replace the reducing end with a reactive primary amine group. It can then be modified with LPS, eritoran or a similar modifier. As another example, the precursor can be a defined oligosaccharide like laminaribiose (2 units), laminaritriose (3 units), laminaritetraose (4 units) or a defined oligosaccharide of any known unit number. The precursor, as another example, can also contain β(1,6) linkages at any (1,3):(1,6) ratio higher than or equal to 1:1. An another example, the precursor can also be a synthesized molecule. For example, the precursor, in some embodiments, is a synthesized β(1,3)-L-glucan.

The molecules of the conjugates provided herein can be conjugated to each other by any physiochemical means. As used herein, "conjugated" means two entities stably bound to one another. It is important that the nature of the attachment be such that it does not impair substantially the effectiveness of the conjugate. Keeping these parameters in mind, any linkage known to those of ordinary skill in the art may be employed including covalent or noncovalent linkage. Covalent linkage, in some embodiments, is preferred. Such means and methods of attachment are well known to those of ordinary skill in the art.

Specific examples of covalent bonds include those wherein bifunctional crosslinker molecules are used. The crosslinker molecules may be homobifunctional or heterobifunctional, depending upon the nature of the molecules to be conjugated. Homobifunctional cross-linkers have two identical reactive groups. Heterobifunctional cross-linkers are defined as having two different reactive groups that allow for sequential conjugation reaction. Various types of commercially available crosslinkers are reactive with one or more of the following groups: primary amines, secondary amines, sulphydryls, carboxyls, carbonyls and carbohydrates. Examples of amine-specific cross-linkers are bis(sulfosuccinimidyl) suberate, bis[2-(succinimidooxycarbonyloxy)ethyl]sulfone, disuccinimidyl suberate, disuccinimidyl tartarate, dimethyl adipimate.2 HCl, dimethyl pimelimidate.2 HCl, dimethyl suberimidate.2 HCl, and ethylene glycolbis-[succinimidyl-[succinate]]. Cross-linkers reactive with sulfhydryl groups include bismaleimidohexane, 1,4-di-[3'-(2'-pyridyldithio)-propionamido)] butane, 1-[p-azidosalicylamido]-4-[iodoacetamido]butane, and N-[4-(p-azidosalicylamido)butyl]-3'-[2'-pyridyldithio] propionamide. Crosslinkers preferentially reactive with carbohydrates include azidobenzoyl hydrazine. Crosslinkers preferentially reactive with carboxyl groups include 4-[p-azidosalicylamido]butylamine. Heterobifunctional cross-linkers that react with amines and sulfhydryls include N-succinimidyl-3-[2-pyridyldithio]propionate, succinimidyl[4-iodoacetyl]aminobenzoate, succinimidyl 4-[N-maleimidomethyl]cyclohexane-1-carboxylate, m-maleimidobenzoyl-N-hydroxysuccinimide ester, sulfosuccinimidyl 6-[3-[2-pyridyldithio]propionamido]hexanoate, and sulfosuccinimidyl 4-[N-maleimidomethyl]cyclohexane-1-carboxylate. Heterobifunctional cross-linkers that react with carboxyl and amine groups include 1-ethyl-3-[[3-dimethylaminopropyl]-carbodiimide hydrochloride (EDC), (1-cyclohexyl-3-(2-morpholinyl-(4)-ethyl) carbodiimide (CMC), N,N'-dicyclohexylcarbodiimide (DCC), N,N'-diisopropryl carbodiimide (DIC). Heterobifunctional cross-linkers that react with carbohydrates and sulfhydryls include 4-[N-maleimidomethyl]-cyclohexane-1-carboxylhydrazide.2 HCl, 4-(4-N-maleimidophenyl)-butyric acid hydrazide.2 HCl, and 3-[2-pyridyldithio]propionyl hydrazide. The cross-linkers are bis-[β-4-azidosalicylamido) ethyl]disulfide and glutaraldehyde.

The carbohydrate-based inhibitors provided herein can be conjugated to a carrier. Such carriers include particles, spheres, capsules, polymers, etc. In some embodiments, the carbohydrate-based inhibitors are conjugated to a particle, such as a microparticle, nanoparticle, dendrimer, etc. The conjugation of the carbohydrate-based inhibitors to a carrier can be conjugated as provided above or as otherwise known to those of ordinary skill in the art.

A number of different techniques exist for making microparticles including phase separation, solvent evaporation, emulsification and spray drying. The following examples are intended to provide guidance in the synthesis of microparticles.

Encapsulated microspheres made from poly(lactide-co-glycolide) and poly(ε-CBZ-L-lysine) and subsequently treated so as to expose surface reactive amino groups have been reported previously (Zheng and Hornsby, 1999, Biotechnol. Prog. 15:763-767). Once the microspheres are formed using double-emulsification/solvent evaporation (Alonso, et al., 1993, Pharmacol. Res. 10:945-953), the carbobenzoxy (i.e., CBZ) protective groups are removed using either acid hydrolysis or lithium/liquid ammonia reduction, thereby exposing reactive amine groups. Lithium/liquid ammonia reduction is recommended if microsphere are desired, given its less harsh effect of the external surface of the microparticle. In addition, the lithium treatment was reported to be more effective in producing surface reactive amino groups than was the acid hydrolysis procedure. If a solid surface particle (i.e., a microsphere) is desired, the lithium treatment may be preferred. In this latter method, the active agent may be added during the formation of the microparticles since the lithium treatment reportedly does not create pores in the surface of the particles and thus will not adversely affect the agent. If, on the other hand, a surface porous particle is desired, then the acid hydrolysis method may be preferred, provided the agent is either resistant to the acid treatment or is loaded into the particles following acid treatment. A similar strategy may be used to produce non-biodegradable microparticles, by substituting poly(lactide-co-glycolide) with a non-biodegradable polymer such as those disclosed herein or otherwise known to those of ordinary skill in the art. Commercially available microparticles include those made from polyacrylamide, polyacrylate, polystyrene, or latex (Bio-Rad Laboratories (Richmond, Calif.), LKB Produkter (Stockholm, Sweden)) or those made from natural polymers such as cellulose, agarose, crosslinked agarose, globulin, and liposomes (Bio-Rad Laboratories (Richmond, Calif.), Pharmacia (Piscataway, N.J.), IBF (France)).

The carrier can also be, but is not limited to, one or a plurality of lipid nanoparticles, polymeric nanoparticles, metallic nanoparticles, surfactant-based emulsions, dendrimers, and/or nanoparticles that are developed using a combination of nanomaterials such as lipid-polymer nanoparticles.

In some embodiments, the carrier can be an acrylic polymer. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly (methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

The compounds provided herein can bind a GNBP and/or inhibit β(1,3)-glucanase activity. In some embodiments, the carbohydrate-based inhibitor does not inhibit β-1,4-glucosidase activity. In other embodiments, the carbohydrate-based inhibitor does not inhibit α-1,4-glucosidase activity. In still other embodiments, the carbohydrate-based inhibitor does not inhibit β-1,4-glucosidase and does not inhibit α-1,4-glucosidase activity. In other embodiments, the carbohydrate-based inhibitor only inhibits β(1,3)-glucanase activity. In another embodiment, the carbohydrate-based inhibitor inhibits β(1,3)-glucanase activity and does not inhibit any other glucanase and/or glucosidase enzymatic activity. In some other embodiments, the compounds do not have cellulase inhibitory activity and/or do not function as a feeding stimulant. In a further embodiment, the carbohydrate-based inhibitor does not inhibit β-1,4-glucosidase, does not inhibit α-1,4-glucosidase activity, does not have cellulase inhibitory activity and does not function as a feeding stimulant. As used herein, a "cellulase inhibitor" is a compound that prevents one or more of the cellulases in the gut of a pest, such as a termite, from digesting cellulose. "Feeding stimulant" refers to compounds that affect the feeding rate of a pest, such as a termite, that increase the amount that pests eat of compositions containing the compound over other compositions and/or their regular food source. In some embodiments, therefore, the compounds provided herein do not also function as a cellulase inhibitor or a feeding stimulant. In some embodiments, the compounds function as a cellulase inhibitor or a feeding stimulant but not both. In all embodiments where the compounds are defined by an activity, for example an enzymatic activity, or function the level of activity or function is compared to the level of activity or function compared to a control. In some embodiments, the control is a negative control, and the level of activity or function is not significantly different from the level of activity or function of the negative control.

In other embodiments, compositions are provided that comprise a carbohydrate-based inhibitor that binds a GNBP and/or inhibits β(1,3)-glucanase activity. In some of these embodiments, the carbohydrate-based inhibitor can also function as a cellulase inhibitor and/or a feeding stimulant; however, in some of these embodiments, the amount of the carbohydrate-based inhibitor in the composition is effective to bind the GNBP and/or inhibit β(1,3)-glucanase activity but is not effective to inhibit cellulase and/or stimulate feeding (i.e., the level of cellulase inhibition and/or feeding stimulation is not significantly different from the level that would be seen with a negative control).

The compounds and compositions provided herein can "protect against or treat pest infestation". The term refers to affecting a pest's ability to infest and, therefore, refers to the inhibition or elimination of pest infestation. The term is also meant to include a reduction in the damage caused by the pest and/or the ability of the pest to infest and/or cause damage. The terms "infest" or "infestation" are generally used interchangeably throughout. Therefore, in the methods as described herein, the pest's ability to infest or maintain an infestation is inhibited or eliminated. "Effective amounts" for achieving any of the desired endpoints described herein, such as protecting against or treating pest infestation refers to any amount that results in any of the above. A skilled person is able to determine such amounts with methods known in the art.

In certain embodiments, the methods can be used to control pests, including insects, such as termites, flies, moths, ants, beetles, mosquitoes, and silk worms, in particular for the protection of plants, wood, seeds (e.g., stored seeds), grain (e.g., stored grain) and/or manmade structures from infestation and/or damage by such pests. As used herein, "manmade structure" refers to any structure made by man that can be damaged by pests. Such, structures are, in some embodiments, made of wood.

The term "pest" as used herein includes a variety of types of pests such as insects. An insect can be any insect that expresses a GNBP, such as a GNBP-1 or GNBP-2 that, in some embodiments, has β(1,3)-glucanase activity. In one embodiment, the insect may belong to the following orders: Acari, Araneae, Anoplura, Coleoptera, Collembola, Dermaptera, Dictyoptera, Diplura, Diptera, Embioptera, Ephemeroptera, Grylloblatodea, Hemiptera, Homoptera, Hymenoptera, Isoptera, Lepidoptera, Mallophaga, Mecoptera, Neuroptera, Odonata, Orthoptera, Phasmida, Plecoptera, Protura, Psocoptera, Siphonaptera, Siphunculata, Thysanura, Strepsiptera, *Spodoptera*, Thysanoptera, Trichoptera, and Zoraptera. The insect may also belong to any of the orders provided below in the Examples.

In preferred, but non-limiting, embodiments of the invention the insect may be one or more of the following:

(1) an insect which is a plant pest, such as, but not limited, to *Nilaparvata* spp. (e.g. *N. lugens* (brown planthopper)); *Laodelphax* spp. (e.g. *L. striatellus* (small brown planthopper)); *Nephotettix* spp. (e.g. *N. virescens* or *N. cincticeps* (green leafhopper), or *N. nigropictus* (rice leafhopper)); *Sogatella* spp. (e.g. *S. furcifera* (white-backed planthopper)); *Blissus* spp. (e.g. *B. leucopterus leucopterus* (chinch bug)); *Scotinophora* spp. (e.g. *S. vermidulate* (rice blackbug)); *Acrosternum* spp. (e.g. *A. hilare* (green stink bug)); *Parnara* spp. (e.g. *P. guttata* (rice skipper)); *Chilo* spp. (e.g. *C. suppressalis* (rice striped stem borer), *C. auricilius* (gold-fringed stem borer), or *C. polychrysus* (dark-headed stem borer)); *Chilotraea* spp. (e.g. *C. polychrysa* (rice stalk borer)); *Sesamia* spp. (e.g. *S. inferens* (pink rice borer)); *Tryporyza* spp. (e.g. *T. innotata* (white rice borer), or *T. incertulas* (yellow rice borer)); *Cnaphalocrocis* spp. (e.g. *C. medinalis* (rice leafroller)); *Agromyza* spp. (e.g. *A. oryzae* (leafminer), or *A. parvicornis* (corn blot leafminer)); *Diatraea* spp. (e.g. *D. saccharalis* (sugarcane borer), or *D. grandiosella* (southwestern corn borer)); *Narnaga* spp. (e.g. *N. aenescens* (green rice caterpillar)); *Xanthodes* spp. (e.g. *X. transversa* (green caterpillar)); *Spodoptera* spp. (e.g. *S. frugiperda* (fall armyworm), *S. exigua* (beet armyworm), *S. litura* (Oriental leafworm), *S. littoralis* (climbing cutworm) or *S. praefica* (western yellowstriped armyworm)); *Mythimna* spp. (e.g. *Mythmna* (*Pseudaletia*) *seperata* (armyworm)); *Helicoverpa* spp. (e.g. *H. zea* (corn earworm), *H. armigera*); *Colaspis* spp. (e.g. *C. brunnea* (grape *colaspis*)); *Lissorhoptrus* spp. (e.g. *L. oryzophilus* (rice water weevil)); *Echinocnemus* spp. (e.g. *E. squamos* (rice plant weevil)); *Diclodispa* spp. (e.g. *D. armigera* (rice hispa)); *Oulema* spp. (e.g. *O. oryzae* (leaf beetle); *Sitophilus* spp. (e.g. *S. oryzae* (rice weevil)); *Pachydiplosis* spp. (e.g. *P. oryzae* (rice gall midge)); *Hydrellia* spp. (e.g. *H. griseola* (small rice leafminer), or *H. sasakii* (rice stem maggot); *Chlorops* spp. (e.g. *C. oryzae* (stem maggot)); *Diabrotica* spp. (e.g. *D. virgifera* (western corn rootworm),

*D. barberi* (northern corn rootworm), *D. undecimpunctata howardi* (southern corn rootworm), *D. virgifera zeae* (Mexican corn rootworm); *D. balteata* (banded cucumber beetle)); *Ostrinia* spp. (e.g. *O. nubilalis* (European corn borer)); *Agrotis* spp. (e.g. *A. ipsilon* (black cutworm)); *Elasmopalpus* spp. (e.g. *E. lignosellus* (lesser cornstalk borer)); *Melanotus* spp. (wireworms); *Cyclocephala* spp. (e.g. *C. borealis* (northern masked chafer), or *C. immaculata* (southern masked chafer)); *Phaedon* spp. (e.g. *P. cochleariae* (mustard leaf beetle)); *Epilachna* spp. (e.g. *E. varivestis* (Mexican bean beetle)); *Popillia* spp. (e.g. *P. japonica* (Japanese beetle)); *Chaetocnema* spp. (e.g. *C. pulicaria* (corn flea beetle)); *Sphenophorus* spp. (e.g. *S. maidis* (maize billbug)); *Rhopalosiphum* spp. (e.g. *R. maidis* (corn leaf aphid)); *Anuraphis* spp. (e.g. *A. maidiradicis* (corn root aphid)); *Melanoplus* spp. (e.g. *M. femurrubrum* (redlegged grasshopper) *M. differentialis* (differential grasshopper) or *M. sanguinipes* (migratory grasshopper)); *Hylemya* spp. (e.g. *H. platura* (seedcorn maggot)); *Anaphothrips* spp. (e.g. *A. obscrurus* (grass thrips)); *Solenopsis* spp. (e.g. *S. milesta* (thief ant)); or spp. (e.g. *T. urticae* (twospotted spider mite), *T. cinnabarinus* (carmine spider mite); *Helicoverpa* spp. (e.g. *H. zea* (corn earworm), or *H. armigera* (cotton bollworm)); *Pectinophora* spp. (e.g. *P. gossypiella* (pink bollworm)); *Earias* spp. (e.g. *E. vittella* (spotted bollworm)); *Heliothis* spp. (e.g. *H. virescens* (tobacco budworm)); *Anthonomus* spp. (e.g. *A. grandis* (boll weevil)); *Pseudatomoscelis* spp. (e.g. *P. seriatus* (cotton fleahopper)); *Trialeurodes* spp. (e.g. *T. abutiloneus* (banded-winged whitefly) *T. vaporariorum* (greenhouse whitefly)); *Bemisia* spp. (e.g. *B. argentifolii* (silverleaf whitefly)); *Aphis* spp. (e.g. *A. gossypii* (cotton aphid)); *Lygus* spp. (e.g. *L. lineolaris* (tarnished plant bug) or *L. hesperus* (western tarnished plant bug)); *Euschistus* spp. (e.g. *E. conspersus* (consperse stink bug)); *Chlorochroa* spp. (e.g. *C. sayi* (Say stinkbug)); *Nezara* spp. (e.g. *N. viridula* (southern green stinkbug)); *Thrips* spp. (e.g. *T. tabaci* (onion thrips)); *Frankliniella* spp. (e.g. *F. fusca* (tobacco thrips), or *F. occidentalis* (western flower thrips)); *Leptinotarsa* spp. (e.g. *L. decemlineata* (Colorado potato beetle), *L. junta* (false potato beetle), or *L. texana* (Texan false potato beetle)); *Lema* spp. (e.g. *L. trilineata* (three-lined potato beetle)); *Epitrix* spp. (e.g. *E. cucumeris* (potato flea beetle), *E. hirtipennis* (flea beetle), or *E. tuberis* (tuber flea beetle)); *Epicauta* spp. (e.g. *E. vittata* (striped blister beetle)); *Empoasca* spp. (e.g. *E. fabae* (potato leafhopper)); *Myzus* spp. (e.g. *M. persicae* (green peach aphid)); *Paratrioza* spp. (e.g. *P. cockerelli* (psyllid)); *Conoderus* spp. (e.g. *C. falli* (southern potato wireworm), or *C. vespertinus* (tobacco wireworm)); *Phthorimaea* spp. (e.g. *P. operculella* (potato tuberworm)); *Macrosiphum* spp. (e.g. *M. euphorbiae* (potato aphid)); *Thyanta* spp. (e.g. *T. pallidovirens* (redshouldered stinkbug)); *Phthorimaea* spp. (e.g. *P. operculella* (potato tuberworm)); *Keiferia* spp. (e.g. *K. lycopersicella* (tomato pinworm)); *Limonius* spp. (wireworms); *Manduca* spp. (e.g. *M. sexta* (tobacco hornworm), or *M. quinquemaculata* (tomato hornworm)); *Liriomyza* spp. (e.g. *L. sativae, L. trifolli* or *L. huidobrensis* (leafminer)); *Drosophila* spp. (e.g. *D. simulans, D. yakuba, D. pseudoobscura, D. virilis* or *D. melanogaster* (fruitflies)); *Atherigona* spp. (e.g. *A. soccata* (shoot fly); *Carabus* spp. (e.g. *C. granulatus*); *Chironomus* spp. (e.g. *C. tentanus*); *Ctenocephalides* spp. (e.g. *C. felis* (cat flea)); *Diaprepes* spp. (e.g. *D. abbreviatus* (root weevil)); *Ips* spp. (e.g. *I. pini* (pine engraver)); *Tribolium* spp. (e.g. *T. castaneum* (red floor beetle)); *Glossina* spp. (e.g. *G. morsitans* (tsetse fly)); *Anopheles* spp. (e.g. *A. gambiae* str. PEST (malaria mosquito) or *A. albimanus* (malaria mosquito); *Acyrthosiphon* spp. (e.g. *A. pisum* (pea aphid)); *Apis* spp. (e.g. *A. melifera* (honey bee)); *Homalodisca* spp. (e.g. *H. coagulata* (glassy-winged sharpshooter)); *Aedes* spp. (e.g. *Ae. aegypti* (yellow fever mosquito)); *Bombyx* spp. (e.g. *B. mori* (silkworm)); *Locusta* spp. (e.g. *L. migratoria* (migratory locust)); *Boophilus* spp. (e.g. *B. microplus* (cattle tick))s *Acanthoscurria* spp. (e.g. *A. gomesiana* (red-haired chololate bird eater)); *Diploptera* spp. (e.g. *D. punctata* (pacific beetle cockroach)); *Heliconius* spp. (e.g. *H. erato* (red passion flower butterfly), *H. melpomene* (postman butterfly) or *H. himera*); *Plutella* spp. (e.g. *P. xylostella* (diamontback moth)); *Armigeres* spp. (e.g. *A. subalbatus*); *Culicoides* spp. (e.g. *C. sonorensis* (biting midge)); *Biphyllus* spp. (e.g. *B. lunatus* (skin beetle)); *Mycetophagus* spp (e.g. *M. quadripustulatus*); *Hydropsyche* spp (caddisflies); *Oncometopia* spp. (e.g. *O. nigricans* (sharpshooter)); *Papilio* spp. (e.g. *P. dardanus* (swallowtail butterfly)); *Antheraea* spp. (e.g. *A. yamamai* (japanese oak silkmoth); *Trichoplusia* spp. (e.g. *T. ni* (cabbage looper)); *Callosobruchus* spp. (e.g. *C. maculatus* (cowpea weevil)); *Rhynchosciara* spp. (e.g. *R. Americana* (fungus gnat)); *Sphaerius* spp. (minute bog beatle); *Ixodes* spp. (e.g. *I. scapularis* (black-legged tick)); *Diaphorina* spp. (e.g. *D. citri* (asian citrus psyllid)); *Meladema* spp. (e.g. *M. coriacea* (Black Predacious Diving Beetle); *Rhipicephalus* spp. (e.g. *R. appendiculatus* (brown ear tick)); *Amblyomma* spp. (e.g. *A. americanum* (lone star tick); *Toxoptera* spp. (e.g. *T. citricida* (brown citrus aphid); *Hister* spp.; *Dysdera* spp. (e.g. *D. erythrina* (cell spider)), *Lonomia* spp. (e.g. *L. obliqua* (caterpillar)); and *Culex* spp. (e.g. *C. pipiens* (house mosquito)): and (2) an insect that causes unwanted damage to substrates or materials, such as insects that attack plants, wood, seeds (e.g., stored seeds), grain (e.g., stored grain), manmade structures, etc. Insect examples of such pests include household insects, ecto-parasites and insects and/or arachnids such as, by way of example and not limitation, flies, spider mites, thrips, ticks, red poultry mite, ants, cockroaches, termites, crickets including house-crickets, silverfish, booklice, beetles, earwigs, mosquitoes and fleas.

The term "insect" encompasses insects of all types and at all stages of development, including egg, larval or nymphal, pupal, and adult stages.

The compositions provided herein can include an additional pesticide. "Pesticide" as used herein includes insecticides, herbicides, and fungicides. Likewise, the methods provided can include a further step of contacting the pest, soil, plant, wood, seeds (e.g., stored seeds), grain (e.g., stored grain) or manmade structure with an additional pesticide. The additional pesticide can be any of the pesticides known in the art. An insecticide is a pesticide used against insects, which include ovicides and larvicides used against the eggs and larvae of insects, respectively. Insecticides include, but are not limited to: (i) organochlorine/organochloride compounds (e.g. Aldrin, Chlordane, Chlordecone, DDT, Dieldrin, Endosulfan, Endrin, Heptachlor, Hexachlorobenzene, Lindane (gamma-hexachlorocyclohexane), Methoxychlor, Mirex, Pentachlorophenol, TDE); (ii) organophosphate compounds (e.g. Acephate, Azinphos-methyl, Bensulide, Chlorethoxyfos, Chlorpyrifos, Chlorpyriphos-methyl, Diazinon, Dichlorvos (DDVP), Dicrotophos, Dimethoate, Disulfoton, Ethoprop, Fenamiphos, Fenitrothion, Fenthion, Fosthiazate, Malathion, Methamidophos, Methidathion, Mevinphos, Monocrotophos, Naled, Omethoate, Oxydemeton-methyl, Parathion, Parathion-methyl, Phorate, Phosalone, Phosmet, Phostebupirim, Phoxim, Pirimiphos-methyl, Profenofos, Terbufos, Tetrachlorvinphos, Tribufos, Trichlorfon and other (acetyl)cholinesterase binding agents; (iii) carbamate insecticide compounds (e.g. Aldicarb, Bendiocarb, Carbofuran, Carbaryl, Fenoxycarb, Methomyl, 2-(1-Methylpropyl)phenyl methylcarbamate; (iv) pyrethroids, Allethrin, Bifenthrin, Cyhalothrin, Lambda-cyhalothrin, Cypermethrin, Cyfluthrin, Deltamethrin, Etofenprox, Fenvalerate, Permethrin, Phenothrin, Prallethrin, Resmethrin, Tetramethrin, Tralomethrin, Transfluthrin; (v) neonicotinoids (e.g. Acetamiprid, Clothianidin, Imidacloprid, Nitenpyram, Nithiazine, Thiacloprid, Thiamethoxam and other synthetic analogues of nicotine; (vi) biological insecticides, e.g. plant-derived biological insecticides, such as, Anabasine, Anethole (e.g. for mosquito larvae), Annonin, *Asimina* (pawpaw tree seeds for lice), Azadirachtin, Caffeine, *Carapa*, Cinnamaldehyde (e.g. for mosquito larvae), Cinnamon leaf oil (e.g. for mosquito larvae), Cinnamyl acetate (e.g. for mosquito larvae), Deguelin, Derris, Derris (rotenone), *Desmodium caudatum* (leaves and roots), Eugenol (for mosquito larvae), Linalool, Myristicin, Neem (Azadirachtin), *Nicotiana rustica* (nicotine), eganum harmala, Oregano oil (for *Rhizopertha dominica* beetle), Polyketide, Pyrethrum, *Quassia*, Tetranortriterpenoid, Thymol (e.g. for mites), and non-plant-derived biological insecticides, such as *Bacillus thuringiensis* (Bt toxin) and other biological insecticides, including products based on entomopathogenic fungi (e.g. *Metarhizium anisopliae*), nematodes (e.g. *Steinemema feltiae*) and viruses (e.g. *Cydia pomonella* granulovirus); and (vii) anti-feedants such as, for example, polygodial. Other insecticides are known in the art and are commercially available for example from agrichemical manufacturers such as Bayer CropScience AG (Monheim am Rhein, Germany), Syngenta (Basel, Switzerland), BASF (Ludwigshafen, Germany), Dow Agrosciences (Indianapolis, Ind.), Monsanto (St. Louis, Mo.), and DuPont (Wilmington, Del.).

The additional pesticide can also be a pathogen to which the pest is susceptible, as the compounds provided herein are thought to adversely affect pest immunity. The term "pathogen" as used herein includes a variety of types of pathogens such as nematodes and fungi. The term "pathogen" as with the term "pest" may imply numerous members from a single species or numerous members from a combination of species. The pathogens include those that are provided below in the Examples.

The pathogen may be a fungus or fungi. The fungus or fungi may be one or more of the following not-limiting list: *Acremoniella* spp., *Alternaria* spp. (e.g. *Alternaria brassicola* or *Alternaria solani*), *Ascochyta* spp. (e.g. *Ascochyta pisi*), *Botrytis* spp. (e.g. *Botrytis cinerea* or *Botryotinia fuckeliana*), *Cladosporium* spp., *Cercospora* spp. (e.g. *Cercospora kikuchii* or *Cercospora zaea-maydis*), *Cladosporium* spp. (e.g. *Cladosporium fulvum*), *Colletotrichum* spp. (e.g. *Colletotrichum lindemuthianum*), *Curvularia* spp., *Diplodia* spp. (e.g. *Diplodia maydis*), *Erysiphe* spp. (e.g. *Erysiphe graminis* f. sp. *graminis*, *Erysiphe graminis* f. sp. *hordei* or *Erysiphe pisi*), *Erwinia armylovora*, *Fusarium* spp. (e.g. *Fusarium nivale*, *Fusarium sporotrichioides*, *Fusarium oxysporum*, *Fusarium graminearum*, *Fusarium germinearum*, *Fusarium culmorum*, *Fusarium solani*, *Fusarium moniliforme* or *Fusarium roseum*), *Gaeumanomyces* spp. (e.g. *Gaeumanomyces graminis* f. sp. *tritici*), *Gibberella* spp. (e.g. *Gibberella zeae*), *Helminthosporium* spp. (e.g. *Helminthosporium turcicum*, *Helminthosporium carbonum*, *Helminthosporium mavdis* or *Helminthosporium sigmoideum*), *Leptosphaeria salvinii*, *Macrophomina* spp. (e.g. *Macrophomina phaseolina*), *Magnaportha* spp. (e.g. *Magnaporthe oryzae*), *Mycosphaerella* spp., *Nectria* spp. (e.g. *Nectria heamatococca*), *Peronospora* spp. (e.g. *Peronospora manshurica* or *Peronospora tabacina*), *Phoma* spp. (e.g. *Phoma betae*), *Phakopsora* spp. (e.g. *Phakopsora pachyrhizi*), *Phymatotrichum* spp. (e.g. *Phymatotrichum omnivorum*), *Phytophthora* spp. (e.g. *Phytophthora cinnamomi*, *Phytophthora cactorum*, *Phytophthora phaseoli*, *Phytophthora parasitica*, *Phytophthora citrophthora*, *Phytophthora megasperma* f. sp. *soiae* or *Phytophthora infestans*), *Plasmopara* spp. (e.g. *Plasmopara viticola*), *Podosphaera* spp. (e.g. *Podosphaera leucotricha*), *Puccinia* spp. (e.g. *Puccinia sorghi*, *Puccinia striiformis*, *Puccinia graminis* f. sp. *tritici*, *Puccinia asparagi*, *Puccinia recondita* or *Puccinia arachidis*), *Pythium* spp. (e.g. *Pythium aphanidermatum*), *Pyrenophora* spp. (e.g. *Pyrenophora tritici-repentens* or *Pyrenophora teres*), *Pyricularia* spp. (e.g. *Pyricularia oryzae*), *Pythium* spp. (e.g. *Pythium ultimum*), *Rhincosporium secalis*, *Rhizoctonia* spp. (e.g. *Rhizoctonia solani*, *Rhizoctonia oryzae* or *Rhizoctonia cerealis*), *Rhizopus* spp. (e.g. *Rhizopus chinensid*), *Scerotium* spp. (e.g. *Scerotium rolfsii*), *Sclerotinia* spp. (e.g. *Sclerotinia sclerotiorum*), *Septoria* spp. (e.g. *Septoria lycopersici*, *Septoria glycines*, *Septoria nodorum* or *Septoria tritici*), *Thielaviopsis* spp. (e.g. *Thielaviopsis basicola*), *Tilletia* spp., *Trichoderma* spp. (e.g. *Trichoderma virde*), *Uncinula* spp. (e.g. *Uncinula necator*), *Ustilago maydis* (e.g. corn smut), *Venturia* spp. (e.g. *Venturia inaequalis* or *Venturia pirina*) or *Verticillium* spp. (e.g. *Verticillium dahliae* or *Verticillium albo-atrum*).

Furthermore, the pathogen may be a nematode or nematodes. The nematode or nematodes may be one or more of the following not-limiting list: Root Knot Nematodes (*Meloidogyne* spp.) in rice (e.g. *M. incognita*, *M. javanica* or *M. graminicola*), in soybean (e.g. *M. incognita* or *M. arenaria*), in cotton (e.g. *M. incognita*), in potato (e.g. *M. chitwoodi* or *M. hapla*), in tomato (e.g. *M. chitwoodi*), in tobacco (e.g. *M. incognita*, *M. javanica* or *M. arenaria*), and in corn (e.g. *M. incognita*); Cyst Nematodes (*Heterodera* spp.) in rice (e.g. *H. oryzae*), in soybean (e.g. *H. glycines*) and in corn (e.g. *H. zeae*); Cyst nematodes (*Globodera* spp.) in potato (e.g. *G. pallida* or *G. rostochiensis*); Reniform Nematodes (*Rotylenchulus* spp.) in cotton (e.g. *R. reniformis*); Root lesion nematodes (*Pratylenchus* spp.) in banana (e.g. *P. coffeae* or *P. goodeyi*); Burrowing Nematodes (*Radopholus* spp.) in banana (e.g. *R. similis*).

The pest, soil, plant, wood, seeds (e.g., stored seeds), grain (e.g., stored grain), or manmade structure can be contacted with the compounds or compositions provided herein in any suitable manner. For example, the pest, soil, plant, wood, seeds (e.g., stored seeds), grain (e.g., stored grain), or manmade structure can be contacted with the compounds or compositions in pure or substantially pure form, for example, an aqueous solution. In this embodiment, the pest, soil, plant, wood, seeds (e.g., stored seeds), grain (e.g., stored grain), or manmade structure may be simply "soaked" with an aqueous solution comprising the compound or composition. In a further embodiment, the pest, soil, plant, wood, seeds (e.g., stored seeds), grain (e.g., stored grain), or manmade structure can be contacted by spraying the pest, soil, plant, wood, seeds (e.g., stored seeds), grain (e.g., stored grain), or manmade structure with a liquid composition. Additional methods will be known to the skilled person.

Alternatively, the compounds or compositions provided may be linked to a food component of the pests in order to increase uptake of the compound or composition by the pest.

The compounds or compositions provided may also be incorporated in the medium in which the pest grows in or on, on a material or substrate that is infested by the pest, or impregnated in a substrate or material susceptible to infestation by the pest.

In another specific embodiment, the compounds or compositions may be, or be used in, a coating that can be applied to a substrate in order to protect the substrate from infestation by a pest and/or to prevent, arrest or reduce pest growth on the substrate and thereby prevent damage caused by the pest. In this embodiment, the composition can be used to protect any substrate or material that is susceptible to infestation by or damage caused by a pest, for example, substrates such as wood. Houses and other wood products can be destroyed by termites, powder post beetles, and carpenter ants. The subterranean termite and Formosan termite are the most serious pests of houses in the southern United States and tropical regions. Any harvested plant can be attacked by insects. Flour beetles, grain weevils, meal moths and other stored product pests will feed on stored grain, cereals, pet food, powdered chocolate, and almost everything else in the kitchen pantry that is not protected. Larvae of moths eat clothes made from animal products, such as fur, silk and wool. Larvae of carpet beetles eat both animal and plant products, including leather, fur, cotton, stored grain, and even museum specimens. Book lice and silverfish are pests of libraries. These insects eat the starchy glue in the bindings of books. Other insects that have invaded houses include cockroaches which eat almost anything. Cockroaches are not known to be a specific transmitter of disease, but they contaminate food and have an unpleasant odor. They are very annoying, and many pest control companies are kept busy in attempts to control them. The most common cockroaches in houses, grocery stores, and restaurants include the German cockroach, American cockroach, Oriental cockroach, and brown banded cockroach.

The nature of the excipients and the physical form of the composition may vary depending upon the nature of the substrate that is desired to treat. For example, the composition may be a liquid that is brushed or sprayed onto or imprinted into the material or substrate to be treated, or a coating that is applied to the material or substrate to be treated. Provided herein are also methods for treating and/or preventing pest infestation on a substrate comprising applying an effective amount of any of the compositions described herein to said substrate.

In another embodiment, the compounds or compositions are used as a pesticide or insecticide for a plant or for propagation or reproductive material of a plant, such as on seeds. As an example, the composition can be used as a pesticide or insecticide by spraying or applying it on plant tissue or spraying or mixing it on the soil before or after emergence of the plantlets.

Any of the compositions provided herein may be formulated to include the active ingredient(s) and all inert ingredients (such as solvents, diluents, and various adjuvants).

Spray adjuvants (additives) can be added to pesticides to enhance the performance or handling of those pesticides. Adjuvant may include surfactants, crop oils, antifoaming agents, stickers, and spreaders. Adjuvants may also include: surfactants (surface-active agent), such as emulsifiers (e.g. to disperse oil in water), wetting agents (e.g. to reduce interfacial tensions between normally repelling substances), stickers (e.g. to cause the pesticide to adhere to the plant foliage and also to resist wash-off), and spreader-stickers (e.g. combined products that provide better spray coverage and adhesion). Crop oils and crop oil concentrates are light, petroleum-based oils that contain surfactant. Antifoam agents (foam suppressants) may be used to suppress foam formed when pesticides are agitated in the spray tank.

Carriers may serve as the diluent for any of the formulations provided herein. The carrier is the material to which a formulated pesticide is added, e.g. for field applications. A carrier may be used to enable uniform distribution of a small amount of formulated pesticide to a large area. Carriers may include liquid, dry and foam carriers. Liquid carriers, e.g. for spray applications, may include water, liquid fertilizers, vegetable oils, and diesel oil. Dry carriers may be used to apply pesticides without further dilution and may include attapulgite, kaolinite, vermiculite, starch polymers, corn cob, and others. Dry fertilizers can also be carriers.

The compositions provided herein can be a sprayable formulation. Sprayable Formulations (with liquid carrier) include: water-soluble liquids (designated S or SL or SC: form true solutions when mixed with water); Water-soluble powders (designated SP or WSP: are finely divided solids that dissolve completely in water); emulsifiable concentrates (designated E or EC: are oil-soluble emulsifiers that form emulsions when mixed with water); wettable powders (designated W or WP: are finely ground solids consisting of a dry carrier (a finely ground hydrophilic clay), pesticide, and dispersing agents, form an unstable suspension when mixed with water); water-dispersible liquids (designated WDL, L, F, AS: are finely ground solids suspended in a liquid system and form suspension when added to water); water-dispersible granules (designated WDG or DF, also called dry flowables, are dry formulations of granular dimensions made up of finely divided solids that combine with suspending and dispersing agents). Sprayable formulations may be in the form of aerosols and may be applied as droplets.

The compositions provided herein can be a dry formulation. Dry Formulations (e.g. for direct application without dilution in a liquid carrier) include: granules (designated G: consist of dry material in which small, dry carrier particles of uniform size (e.g. clay, sand, vermiculite, or corn cob; with a granule size of e.g. less than 0.61 cubic inches) are impregnated with the active ingredient, and may be applied with granular applicators); pellets (designated P: are dry formulations of pesticide and other components in discrete particles usually larger than 0.61 cubic inches, and may be applied e.g. by hand from shaker cans or with hand spreaders for spot applications). Dry formulations may also be applied as a fine powder or dust.

In yet another embodiment, a method for treating and/or preventing insect growth and/or insect infestation of a plant or propagation or reproductive material of a plant, comprising applying an effective amount of any of the compounds or compositions herein described to a plant or to propagation or reproductive material of a plant.

The compounds or compositions provided may be in any suitable physical form for application to pests, to substrates, to cells, or administration to organisms susceptible to infestation or infected by pests.

In other embodiments, the compositions provided contain further excipients, diluents, or carriers.

The compositions of the invention can include various amounts of the compounds. For example, the compound can be present in an amount of between about 0.000001%-99% by weight of the composition (W/W), preferably 0.00001%-99% by weight (W/W), more preferably, 0.0001%-99% by weight (W/W), still more preferably 0.0002%-99% by weight (W/W). The referenced amounts can be applied or administered in one or more applications or doses given over time.

The methods of the invention can find practical applications in any area of technology where it is desirable to inhibit viability, growth, development, or reproduction of a pest. Particularly useful practical applications include, but are not limited to, (1) protecting plants against pest infestation; (2) protecting materials against damage caused by pests; and (3) generally any application wherein pests need to be controlled and/or wherein damage caused by pests needs to be reduced or prevented.

The compounds provided herein or subparts thereof may be obtained from natural sources, such as from naturally occurring organisms, recombinant organisms, synthetic methods, or any combination thereof.

The invention also provides kits that include containers of the compounds or compositions described herein. It is contemplated that the compounds or compositions may be supplied as a "kit-of-parts" comprising the compound or subpart thereof in one container and an amount of a compound, subpart thereof, or a carrier in a second container and, optionally, one or more suitable diluents for the foregoing components in one or more separate containers. In these embodiments, the compounds, subparts, carriers, or other molecules may be supplied in a concentrated form, such as a concentrated aqueous solution. It may even be supplied in frozen form or in freeze-dried or lyophilized form. The latter may be more stable for long term storage and may be defrosted and/or reconstituted with a suitable diluent immediately prior to use.

Containers, as used herein, includes receptacles of any shape or form that may be made of any suitable material, such as plastic, glass, metal, styrofoam, cardboard and the like, or any combination of such materials.

The kit may be supplied with suitable instructions for use. The instructions may be printed on suitable packaging in which the other components are supplied or may be provided as a separate entity, which may be in the form of a sheet or leaflet for example. The instructions may be rolled or folded for example when in a stored state and may then be unrolled and unfolded to direct use of the remaining components of the kit.

Also provided herein are methods of engineering plants to produce or produce in greater amounts (i.e., overexpress) one or more enzymes that can control the production of a carbohydrate-based inhibitor that binds a GNBP and/or inhibits $\beta(1,3)$-glucanase activity. In these methods, generally, the carbohydrate-based inhibitor is a product of a biosynthetic pathway, and the enzyme is one that can affect the production of the carbohydrate-based inhibitor and/or the amount of the carbohydrate-based inhibitor produced in the plant. The plants are engineered to express or overexpress the one or more enzymes such that a carbohydrate-based inhibitor is produced in the plant in an amount effective to protect against or treat pest infestation. Such plants, as a result, can, in some embodiments, not require the use of exogenous pesticides or insecticides to protect against or treat pest infestation.

As an example, the carbohydrate-based inhibitor can be GDL, and a plant can be engineered to produce or produce in greater amounts an enzyme that is involved in the biosynthetic pathway of GDL. An "enzyme involved in the biosynthetic pathway of GDL" is any enzyme that controls the production of GDL or the amount of GDL that is ultimately produced in the plant. Examples of such enzymes include glucose oxidase. In one embodiment, therefore, the plant is engineered to express glucose oxidase ($\beta$-D-glucose:oxygen 1-oxido-reductase, EC 1.1.3.4, structure pdb77_1). The sequence of the enzyme is known in the art. For example, the sequence of glucose oxidase is known from *Aspergillus niger* and can be cloned from that fungus, as an example. In addition, as the oxidation of glucose using FAD as a cofactor generates hydrogen peroxide, in some embodiments, the enzyme, such as glucose oxidase, can be expressed along with superoxide dismutase or some other radical-eliminating enzyme under the same or a different promoter. The methods provided herein, therefore, in some embodiments, include the step of engineering the plant to express or overexpress superoxide dismutase in addition to glucose oxidase.

The plants suitable for such engineering include any plants for which the protection against or treatment of a pest infestation would be of some benefit. Such plants include agricultural plant species, such as species of rice, corn, wheat, barley, sorghum, etc. Such plants also include soybean, cotton, potato, pea, lettuce, tomato, tobacco, and banana species. Further non-limiting examples, include any of the plants recited herein or any plants that can be affected by infestation of any of the pests provided herein.

Therefore, plants engineered according to the methods provided herein are also provided as are the vectors and plasmids (i.e., vectors and plasmids that include the sequence encoding glucose oxidase and/or superoxide dismutase) for engineering said plants. In some embodiments, the vectors and plasmids further include a promoter that controls the expression of glucose oxidase and/or superoxide dismutase. In some embodiments, the vectors and plasmids can further comprise a selectable marker.

In some embodiments, the methods include the step of introducing a gene, such as the gene encoding glucose oxidase, into one or more plant cells and obtaining a plant, plant tissue or plant cell that can express or overexpress the gene. In other embodiments, the method further includes growing a whole plant from the plant, plant tissue or plant cell that can express or overexpress the gene.

There are a number of methods that can be used to produce a transgenic plant. For example, one method is the "Gene Gun" method (also known as microprojectile bombardment or biolistics). This technique has been useful in transforming, for example, monocot species like corn and rice. Another method is the *Agrobacterium* method. Transformation has been accomplished via *Agrobacterium* in a number of kinds of plants (e.g., in dicots, such as broadleaf plants like soybeans and tomatoes and in monocots, such as grasses and their relatives). *Agrobacterium tumefaciens* is a species of soil-dwelling bacteria that has the ability to infect plant cells with a piece of its DNA. When the bacterial DNA is integrated into a plant chromosome, it can effectively hijack the plant's cellular machinery and use it to ensure the proliferation of the bacterial population. *A. tumefaciens* can infect a plant through wounds. The DNA can enter the plant cell through the wound and move from the cytoplasm to the nucleus and become integrated into the plant chromosome. To harness *A. tumefaciens* as a transgene vector, the tumor-inducing section can be removed, while retaining the border regions and the vir genes.

Selection of successfully transformed plants, plant tissues or plant cells can then be performed following the gene insertion process. Plants, plant tissues or plant cells can be transferred to a selective medium containing, for example, an antibiotic or herbicide, depending on whether and which selectable marker is used. For example, in some embodiments, plants, plant tissues or plant cells expressing the selectable marker gene will survive, and it is assumed that these plants, plant tissues or plant cells possess the transgene of interest. To obtain whole plants from plant cells or plant tissues, for example, the plant cells or plant tissues can be grown under controlled environmental conditions in a series of media containing nutrients and hormones. Once whole plants are generated and produce seed, the progeny can be evaluated.

Other methods for producing transgenic plants can be found in Transgenic Plants: Methods and Protocols (Methods in Molecular Biology), Humana Press, 2004 or are otherwise known to those of ordinary skill in the art.

EXAMPLES

Materials and Methods

Study Species

*N. corniger* nests were collected from Gamboa in the Republic of Panama. The termites in their carton nests were maintained in plastic boxes at 28° C. and 75% humidity and provided with birch wood and water ad libitum.

Bioinformatic Analysis

Insect GNBPs were identified with BLAST search using *Nasutitermes* GNBPs (DQ058898-058922). Representative GNBPs were aligned with ClustalX (35). The phylogenetic tree was constructed by distance analysis with PAUP* version 4.0b10 (36). The tree was rooted with protein sequence from *Bacillus circulans* β(1,3)-glucanase (AAC60453). 1000 replicates were used to calculate bootstrap values and branches were collapsed with a 50% consensus rule.

Termite Extracts, Tissue Samples, Cuticular Washes and Hemocytes

*N. corniger* workers, large workers or soldiers (whole termites or isolated tissues) were surface sterilized (brief wash with 5% hypochlorite and 3 washes with sterile water) and homogenized in acetate buffer (200 mM, pH 5.0, 4 µL/termite) with Biomasher® columns (pore size 80-145µ, Cartagen, San Carlos, Calif.) according to the manufacturer's instructions. Cuticular washes were prepared by gently agitating chilled workers in 0.1% Tween 80 for 5 seconds (10 µL/worker). Wash samples were concentrated with a P10 Microcon® filter (Millipore, Billerica, Mass.). Termite hemocytes were collected from hemolymph drawn from 10 chilled *N. corniger* workers (1 µL/termite) using a micropipette and kept in ice-cold Burns-Tracy saline as described previously (37). Whole cell preparations were obtained by gentle trituration of termites in ice-cold Burns-Tracy saline.

Flow Cytometry

Figure 2:
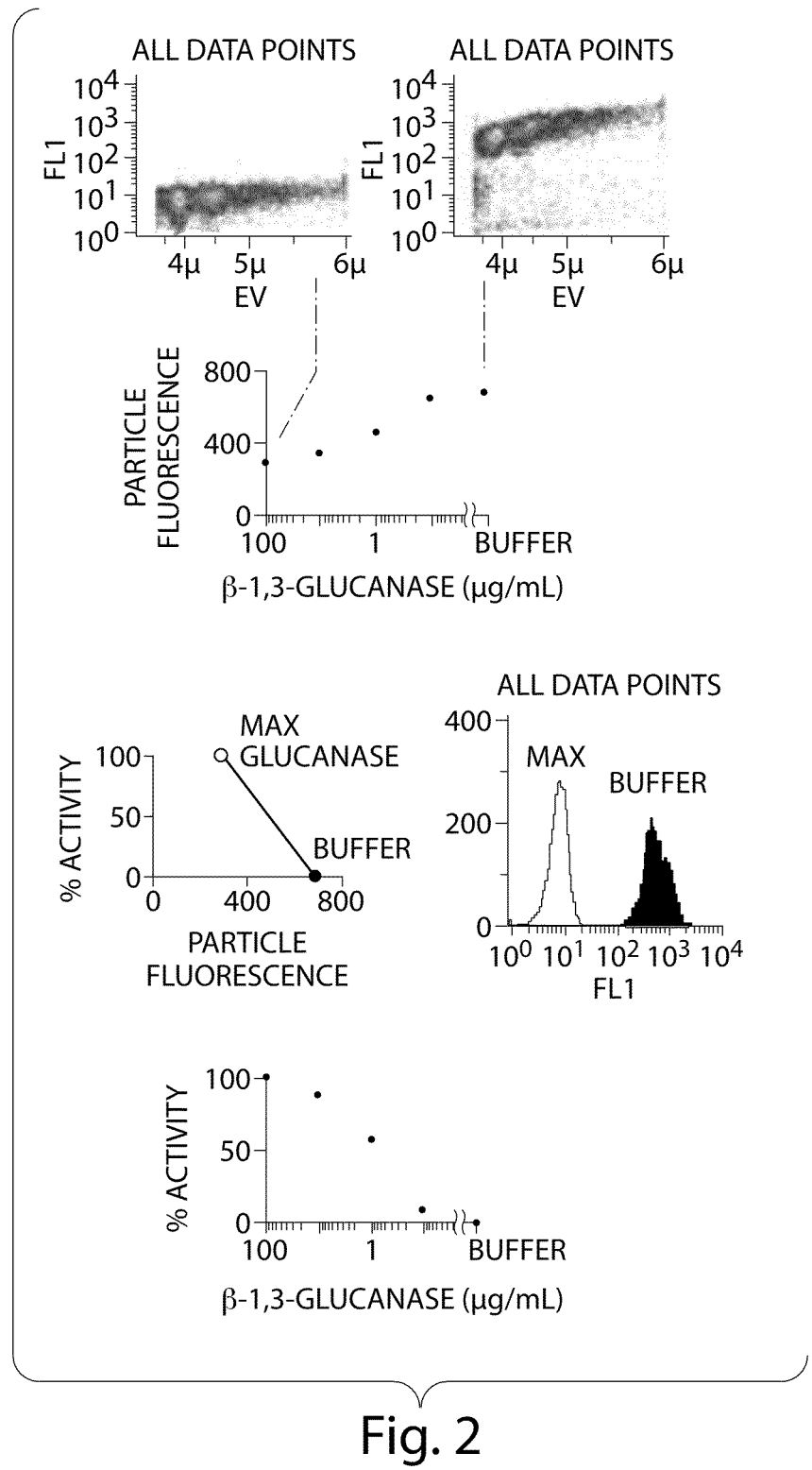
FIG. 2 provides results from a microsphere-based flow cytometric assay for $\beta(1,3)$-glucanase activity. Laminarin was labeled at the reducing end with rhodamine green X-succinyl ester, stably adsorbed on 3.0μ-diameter polystyrene microspheres in carbonate/bicarbonate buffer at pH=9.6 and washed in 100 mM sodium acetate pH 5.5. Samples were then incubated with the fluorescent microspheres for varying time periods starting from 15 min and analyzed by flow cytometry. Purified $\beta(1,3)$-glucanase at 100 μg/mL (0.1 mU/mL) and sodium acetate buffer alone were used as positive and negative controls, respectively. Finally, fluorescence data were transformed to % activity and plotted vs. samples or concentrations.

Hemocyte staining was performed in 0.1% w/v BSA, 0.01% w/v $NaN_3$ in PBS, 30 min on ice per antibody with a single wash with buffer between antibodies (38). Primary antibodies: anti-tGNBP-2 (5 µg/mL) or rabbit IgG (5 µg/mL, Sigma, St. Louis, Mo.); secondary antibody: anti-rabbit PE (1:400, Invitrogen, Carlsbad, Calif.). Intracellular flow cytometry for protein phosphorylation was performed as described (38) with slight modifications. Cells were fixed with 2% v/v formaldehyde, washed and permeabilized in 5% w/v BSA, 1% v/v rabbit serum, 0.1% w/v saponin, 10 mM HEPES, 0.05% w/v $NaN_3$ in PBS, pH 7.4 for 10 minutes on ice. Primary antibody: anti-phospho SAPK/JNK, cross-reactive with termites (FIG. 1, 1:100, Cell Signaling, Beverly, Mass.); secondary antibody: anti-rabbit:fluorescein (1:400, Invitrogen). Flow cytometry was performed on a Beckman-Coulter Cell Lab Quanta™ SC MPL-automated flow cytometer and analyzed with Quanta Analysis™ software.

β(1,3)-Glucanase Assays

β(1,3)-glucanase activity was measured by a gel electrophoresis assay (39) and by a flow cytometric method developed (FIG. 2). Briefly, samples were run on Carboxymethyl Curdlan REmazol Brilliant Blue (CN-Curdlan-RBB, Lowe Biochemica, Germany). Laminarin (Sigma) was labeled with rhodamine green-X succinyl ester (Invitrogen) as described (40), and adsorbed on 3.0µ diameter polystyrene microspheres (Polysciences, Warrington, Pa.) by a 3-hour incubation in carbonate/bicarbonate buffer (50 mM, pH 9.6) at 37° C. Microspheres were then washed and reconstituted in sodium acetate (0.1M, pH 5.5). Samples were mixed with 1 µL of the microsphere suspension, incubated for 15-30 minutes at 37° C. and analyzed by flow cytometry. Commercially available purified β(1,3)-glucanase from *Helix pomatia* or *Bacilus subtilis* was used at 0.1 mU/mL as positive control and results were expressed as % activity of this control.

Antifungal Assays

*M. anisopliae* conidia were incubated with single insect extracts (or the equivalent of a single insect from extract prepared from 8-10 pooled workers) in sodium acetate (50 mM, pH 5.0) containing 0.025% Tween 80 and 50 µg ampicillin (40 µL incubation mix included approximately 100 conidia and crude extract corresponding with one termite). This mix was incubated for 18-24 hours at 25° C., then plated onto potato dextrose agar 100×15 mm plates and supplemented with 50 µg/mL ampicillin CFUs were counted following a 4-day incubation at 25° C. Femtoliter changes in conidial cell volume were directly measured by flow cytometry.

Size Exclusion HPLC and Protein Detection

Extract from 30 termites diluted 1:1 in sodium acetate (0.1M, pH 5.5) was injected into YMC Pack Diol 200 column (300×8 mm ID, particle size 5µ, pore size 20 nm, YMC, Milford, Mass.) and separated on an Agilent 1100 Series instrument at 1 mL/min Fraction content was adsorbed on 3.0µ diameter polystyrene microspheres by a 3-hour incubation in boric acid (0.1M, pH 8.5) followed by 3 washes in cold PBS, the microspheres were stained using anti-tGNBP-2 as described and analyzed by flow cytometry.

Peptide MS

Termite extract was diluted with ultrapure water and analyzed on a Voyager DE matrix-assisted laser desorption/ionization mass spectrometer (Applied Biosystems, Forest City, Calif.) in positive linear mode with α-cyano-4-hydroxycinnamic acid (CHCA) as matrix (30% 10 mg/mL CHCA, 70% acetonitrile), accelerating voltage 20 KV, grid voltage 95%, guide wire 0.05%, extraction delay 75 nsec.

Immunoprecipitation and Western Blots

Anti-tGNBP-2 antibodies were raised in rabbits and purified by standard methods (GenScript, Piscataway, N.J.). Antibodies were covalently linked to 1.0µ diameter Dynabeads® MyOne™ carboxylic acid functionalized magnetic beads (Invitrogen) according to the manufacturer's instructions. Fresh termite extract was diluted 1:1 with IP buffer (25 mM Tris-HCl pH 7.6, 150 mM NaCl, 1% v/v NP-40, 1% v/v protease inhibitor cocktail), and incubated with beads for 1 hour at RT. Beads were isolated, washed with IP buffer, and eluted with a commercial neutral pH buffer (Pierce, Rockford, Ill.). Eluate was desalted and concentrated using a centrifugal column (Vivaspin 10K, Sartorius, Goettingen, Germany) and reconstituted in sodium acetate (0.1M, pH 5.5). SDS-PAGE and western blots were performed and developed by standard procedures; loading amounts were validated by BCA assay. Anti-tGNBP-2 was used at 2.5 µg/mL followed by anti-rabbit HRP (Cell Signaling) at 1:1000. Blots were visualized on a Kodak ImageStation 2000R. Soil samples A and B were collected from two different locations in Boston, USA (*Reticulitermes* sp. inhabiting these locations exhibited positive β(1,3)-glucanase activity).

Homology-Based Structural Modeling of tGNBP-2

The template structure of an endo β(1,3)-glucanase from alkaliphilic *Nocardiopsis* strain F96 (PDB ID: 2hyk) was chosen by the SWISS-MODEL auto homology modeling web portal to construct a structural model for tGNBP-2. The binding of β(1,3)-glucan was investigated by docking a representative β(1,3)-glucan containing tetrasaccharide obtained from its co-crystal structure with a *Bacillus macerans* endo β(1,3)-glucanase (PDB ID: 1U0A) to the active site containing the consensus β(1,3)-glucanase sequence. The binding coordinates of eritoran (an LPS analog) were obtained from its co-crystal structure with Toll-like Receptor 4/MD2 complex (PDB ID: 2Z65).

Combinatorial Cytotoxicity Mapping

Samples of *M. anisopliae* conidia in sodium acetate (0.1M, pH 5.5) were incubated in 384 well plates with samples from HPLC fractions in different combinations (F1+F1, F1+F2, F1+F3 . . . F2+F2, F2+F3 . . . F3+F3 . . . , 10 µL of each fraction) overnight at 25° C. and analyzed by flow cytometry. tGNBP-2 was depleted from 250 µL of each fraction as described above, and supernatants were collected and used for the assay.

In-Vitro Binding Assays

Isolated tGNBP-2 or rhCD14 (R&D Systems, Minneapolis, Minn.) were linked to 3.0µ diameter polystyrene beads (Polysciences) by a 3-hour incubation in boric acid (0.1M, pH 8.5) followed by 3 washes in cold PBS containing 0.1% v/v rabbit serum. Formaldehyde-inactivated pathogenic strains were labeled with FITC as previously described (41). Beads were incubated with labeled pathogens in buffer at 37° C. for 30 minutes and analyzed by flow cytometry. For interference assays, tGNBP-2-adsorbed beads were incubated with either LPS or laminarin at various concentrations, then directly stained with FITC-labeled LPS (Sigma) and analyzed by FACS.

In-Vivo Pin Prick Infection Assay 10 workers were cooled on ice and pricked with a sterilized insect pin immersed in a solution of either *M. anisopliae* or *S. marcescens*. Termites were then released at RT for specific time intervals of 1.5 and 2.5 hours. The experiment was terminated by extracting the termites and freezing the extract for analysis. Groups of cooling alone or cooling+pricking were used as controls.

In-Vivo Survival and Exposure Assays

Conidia (approx. $3 \times 10^7$/mL) were centrifuged at 12,000×g for 1 minute and then suspended in 600 µL 0.1% Tween 80 by vortexing. Two groups of 12 large workers were exposed to filter paper (Watman 5) moistened with these suspensions in 35×15 mm petri dishes for 20 hours. The filter paper was replaced with sterile water-moistened filter paper and dead termites were removed after a daily census of survivorship. tGNBP-2 treatment was performed with conidia suspended in a sample of the immunoprecipitated protein overnight at 25° C., followed by extensive washing in PBS containing 0.1% Tween 80. Dead termites were removed daily, surface sterilized with 70% ethanol and incubated in sterile plates at RT for 4 days for post mortem analysis. For exposure to laminarin or LPS, filter papers were moistened with 300 µL of 0.5 mg/mL or 5 mg/mL solutions of either carbohydrate. Termites were kept on moist filter paper for 24 hours prior to exposure with conidia ($10^7$/mL). Controls included termites that were not exposed to sugars and/or conidia (0.1% Tween 80).

Statistical Analysis and Significance of Survival Data

Data were analyzed by Mann-Whitney U test and Wilcoxon Signed Rank tests with Bonferroni corrections for multiple testing. Termite survival data were analyzed by Cox Regression Analysis. Flow histogram SDs were calculated using software produced half-peak coefficients of variance (% HPCV×mean). Data are presented as means±SD.

Results and Discussion

Termites Express $\beta(1,3)$-Glucanase Activity

Figure 3A:
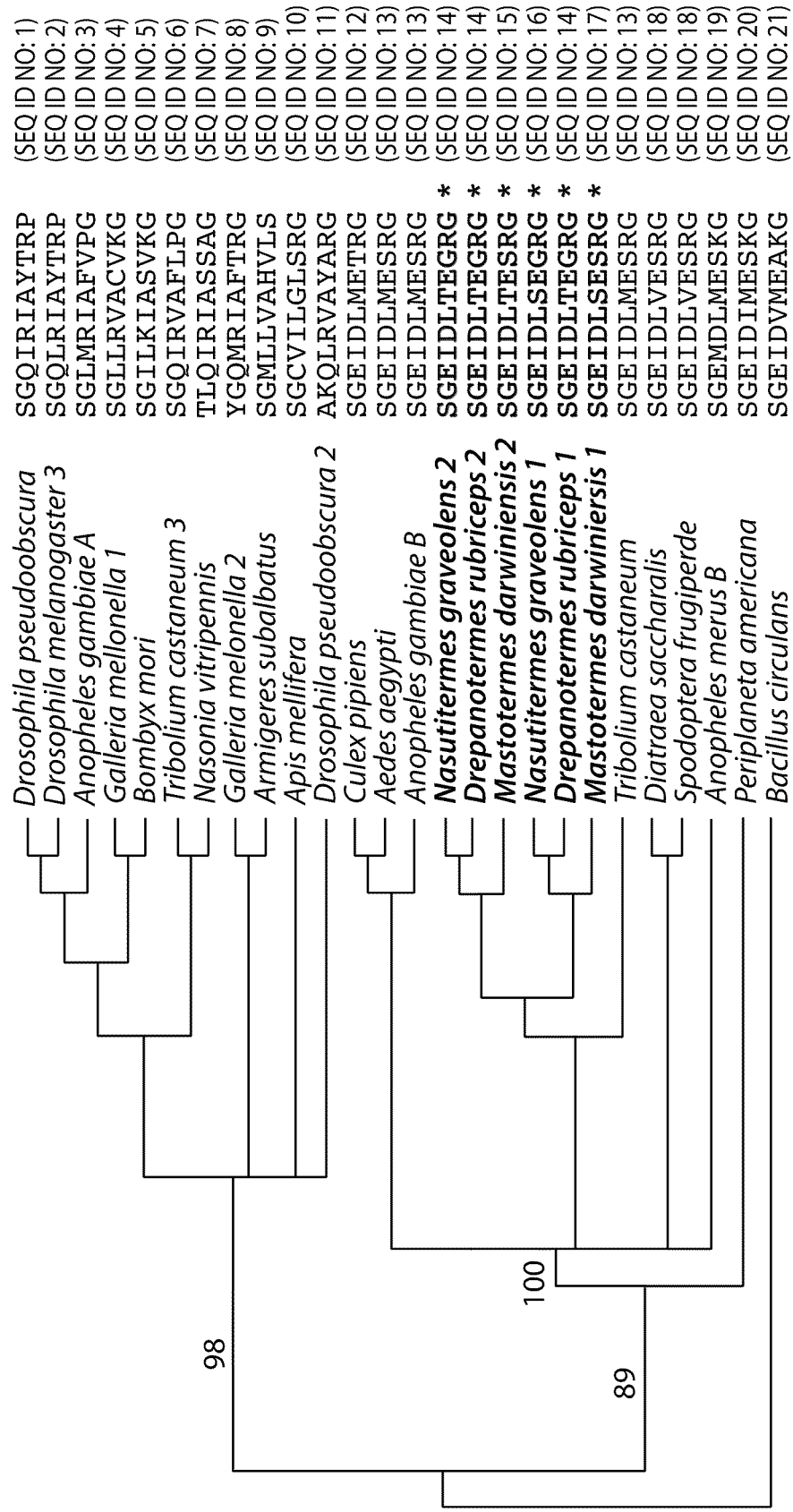
FIG. 3A provides a distance tree of insect GNBPs rooted with *B. circulans* $\beta(1,3)$-glucanase. Numbers depict bootstrap values for basal lineages. Glucanase motif sequences are adjacent to species name. Termite species are marked with an asterisk. Numbers following species name indicate GNBP-1, 2 etc.

Termite GNBPs were positively selected following a single duplication event prior to the divergence of *Mastotermes*, the most ancient lineage of the Isoptera. Adaptive evolution in termite GNBPs appears to have been driven by a co-evolutionary race as well as shifts in habitat that have likely exposed termites to new groups of pathogenic microorganisms. However, sequence analysis of GNBPs from various termite lineages showed that the critical residues involved in the $\beta(1,3)$-glucanase activity remained surprisingly intact (FIG. 3A). Interestingly, the catalytic site appears to have been maintained in the GNBPs of several other insects and their phylogenetic distribution suggests that GNBPs cluster in discrete groups that have either maintained or lost $\beta(1,3)$-glucanase activity (FIG. 3A).

Figure 3B:
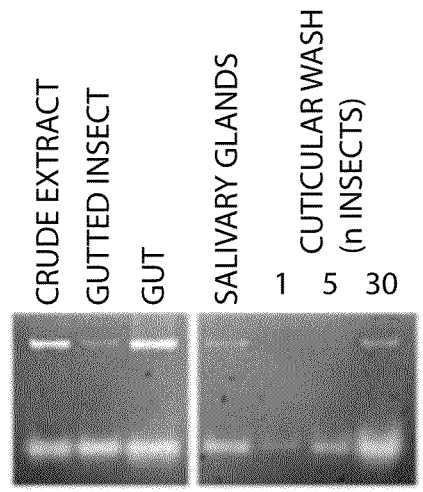
FIG. 3B shows that $\beta(1,3)$-glucanase activity in termite tissues and cuticular washes, assayed on CM-curdlan-RBB gels, was detected (lanes: 1, soldier; 2, large worker; 3, large worker; 4, 10 workers; 5-7, 1, 5 and 30 large workers, respectively).
Figure 3C:
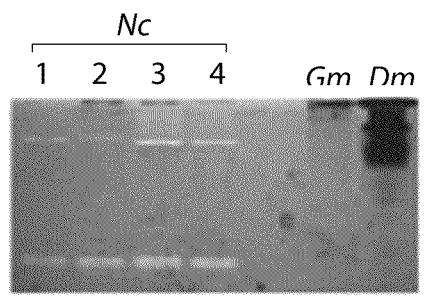
FIG. 3C provides a comparison of activity in extracts from termites (1, *N. corniger* collected from Florida, USA; 2-4, *N. corniger* collected from different colonies in Panama), *D. melanogaster* and *G. mellonella*.

Measurement of $\beta(1,3)$-glucanase activity in *Nasutitermes corniger*, performed by electrophoresis on a chromogenic substrate gel, revealed significant activity in various body tissues and secretions including salivary glands and cuticular washes (FIG. 3B). Other termite species (*Z. augusticollis, C. secundus* and *R. flavipes*) also showed robust $\beta(1,3)$-glucanase activity. This activity was demonstrated by all castes. Other insects, like the ant *Camponotus pennsylvanicus* and the solitary insects *Galleria mellonella* and *Drosophila melanogaster* (FIG. 3C) had no activity. Still, this activity is not limited to termites as suggested by the sequence analysis, and as reported for several pest species (16-18).

Figure 3D:
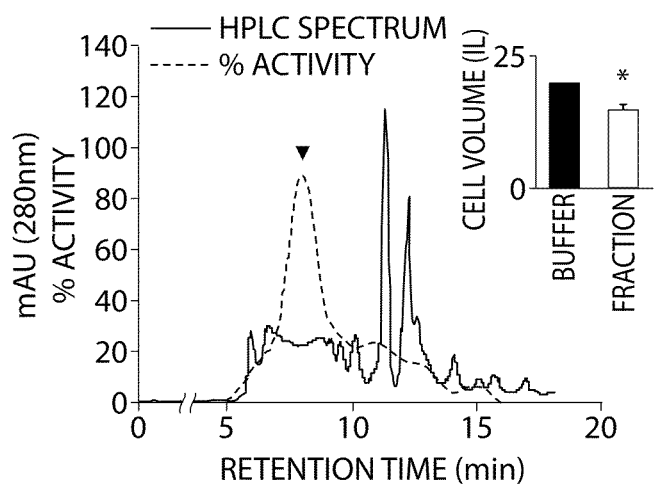
FIG. 3D provides an activity profile of fractionated termites separated by HPLC, and the cytotoxic effect of the peak active fraction ('Fraction', marked with an arrowhead) from termites on *M. anisopliae* conidia, measured by flow cytometry as the effect on cell volume in femtoliters (*, $p<0.05$ vs. Buffer).

The fungal entomopathogen *Metarhizium anisopliae* is a natural termite pathogen and is currently being developed for the biological control of termites and other insect pests (19). Among fungal entomopathogens, *Metarhizium anisopliae* is a significant threat to subterranean termites, constructing their nests and foraging galleries in the soil, because it is a ubiquitous soil pathogen that can evade the immune system once it has entered its host (Wang and St Leger 2006, *Proc. Natl. Acad. Sci. USA* 103: 6647-52). *M. anisopliae* conidia treated with $\beta(1,3)$-glucanases purified from either *Helix pomatia* or *Bacilus subtilis* collapsed due to turgor pressure loss and leakage of intracellular components. Similarly, conidia treated with a termite protein size-exclusion fraction coinciding with peak $\beta(1,3)$-glucanase activity likewise collapsed, and their cell volume decreased by 25% (FIG. 3D, cell volume reduction shown in inset graph).

Figure 4A:
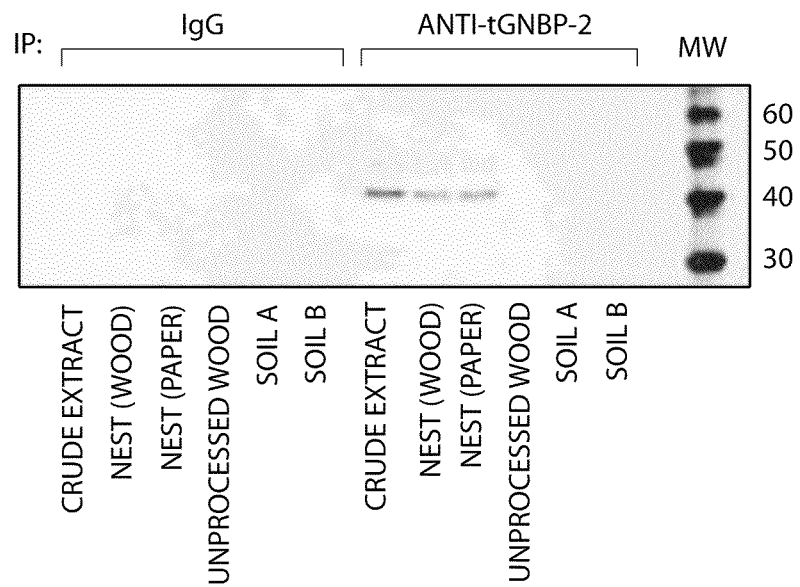
FIG. 4A demonstrates the immunoprecipitation (IP) of tGNBP-2 from termite extracts, nests, unprocessed wood and soils A and B sampled from different locations.
Figure 4B:
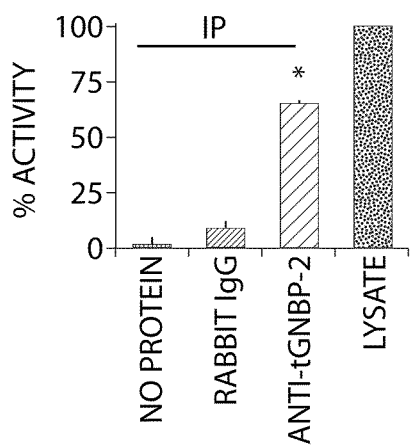
FIG. 4B shows the $\beta(1,3)$-glucanase activity of termite immunoprecipitates isolated by rabbit IgG or anti-tGNBP-2 (*, $p<0.05$ vs. No protein and rabbit IgG).
Figure 4C:
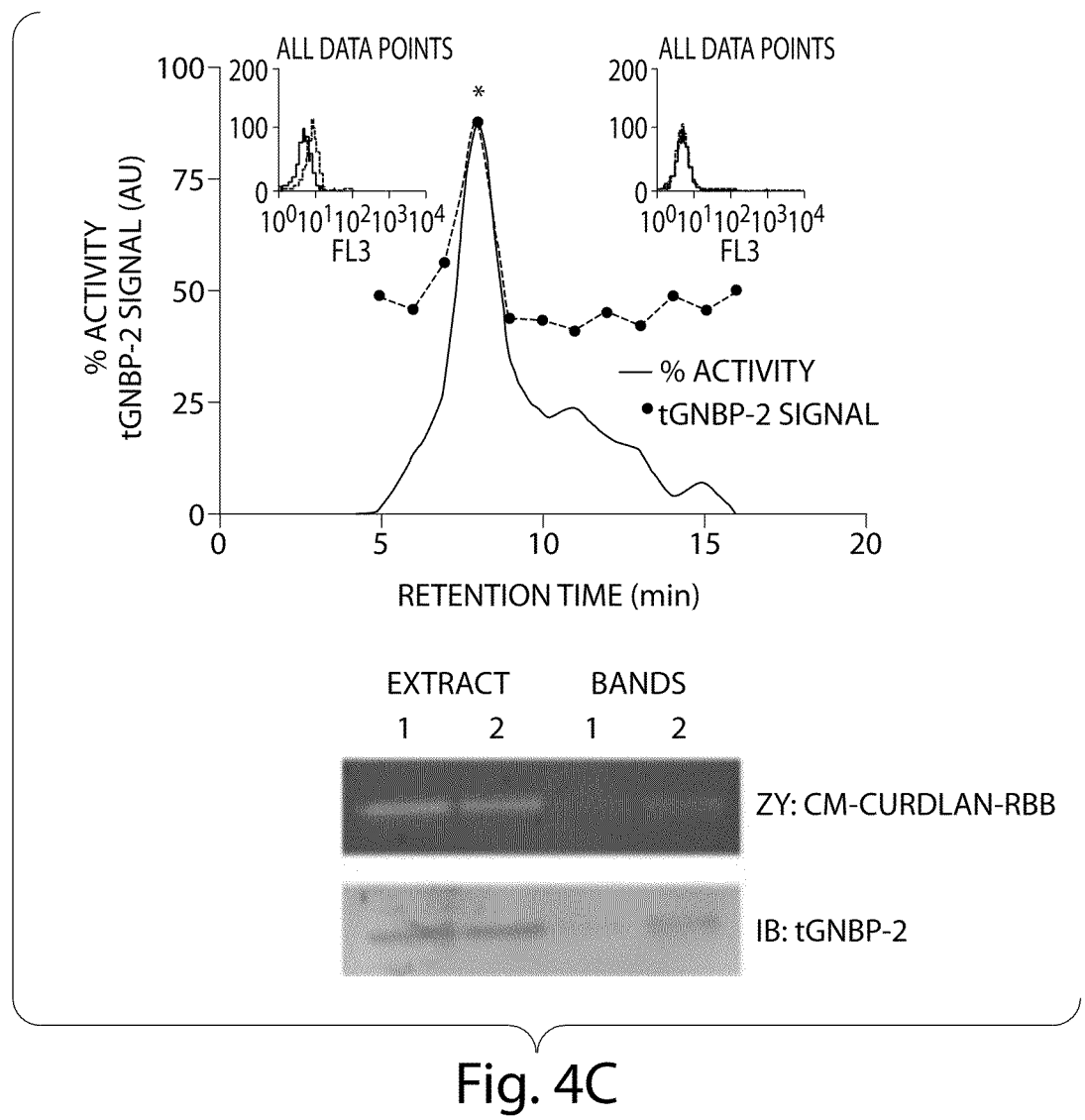
FIG. 4C shows that tGNBP-2 coincides with $\beta(1,3)$-glucanase activity in termites, as measured by flow cytometry (AU=10×[mean fluorescent intensity]; *, $p<0.05$ vs. adjacent fractions) and zymography/Western blot (ZY, zymogram; IB, blot; Bands, samples isolated from excised positive bands in a zymogram). Inlays depict representative histograms used to calculate signal intensities.
Figure 4D:
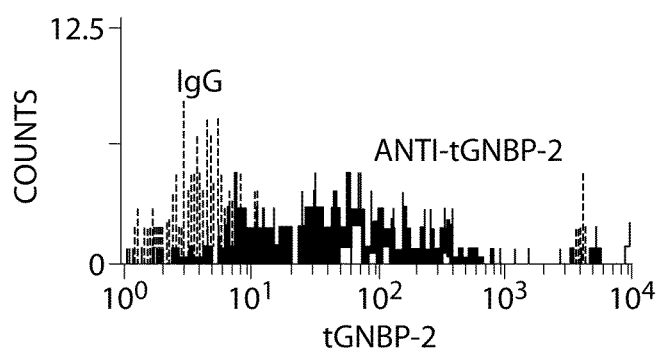
FIG. 4D shows the expression of tGNBP-2 on hemocyte surface, measured by flow cytometry.

Termite GNBP-2 is an Active $\beta(1,3)$-Glucanase Induced by Pathogenic Patterns To associate a termite GNBP with the observed activity, antibodies were raised against termite GNBP-1 and -2 (tGNBP-1 and tGNBP-2, respectively). Native, tGNBP-2 was successfully isolated and purified by immunoaffinity chromatography from both termite extract and nests built from various materials (FIG. 4A). The protein exhibited robust $\beta(1,3)$-glucanase activity (FIG. 4B) and was found to be expressed on the surface of two distinct hemocyte populations, granular hemocytes (Electronic Volume$^{lo}$/Side Scatter$^{hi}$) and large, less dense hemocytes (Electronic Volume$^{lo}$/Side Scatter$^{hi}$, presumably plasmatocytes). No equivalent proteins were precipitated from soil or wood. tGNBP-2 in termite HPLC fractions with peak $\beta(1,3)$-glucanase activity was also detected (FIG. 4C) and on the surface of termite hemocytes (FIG. 4D). The hydrophobic tail of tGNBP-2 is highly homologous to the tail of *Drosophila* GNBP (20), and, therefore, likely serves as a glycosylphosphatidylinositol (GPI) anchor. Existence in both soluble and membrane-associated forms is common among pattern receptors including mammalian CD14 (21) and various insect proteins (22).

Figure 4E:
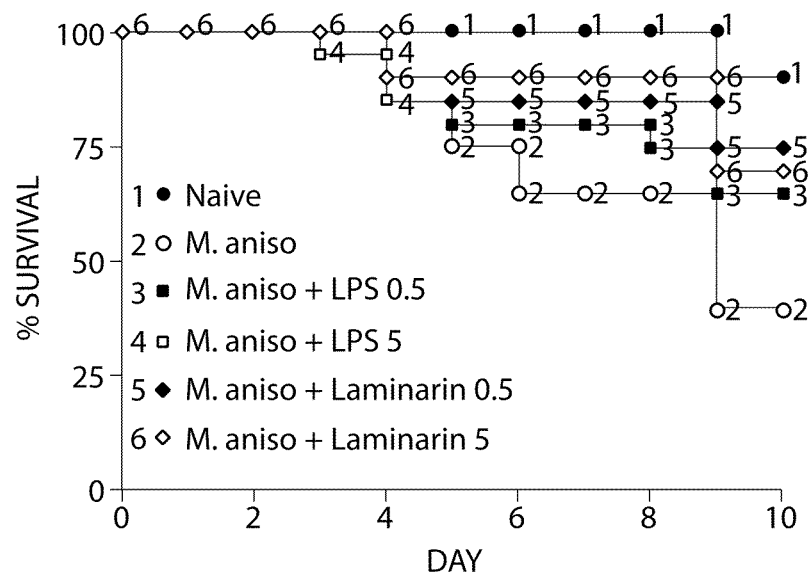
FIG. 4E demonstrates the survival of termites infected with *M. anisopliae* (*M. aniso*) following immunization with LPS or laminarin at either 0.5 or 5 mg/mL along a course of 10 days (mean of 2 groups, n=12/group; all immunized termite groups were $p<0.05$ vs. *M. aniso* only, and $p>0.05$ vs. naive termites with the exception of 0.5 mg/mL LPS).
Figure 4F:
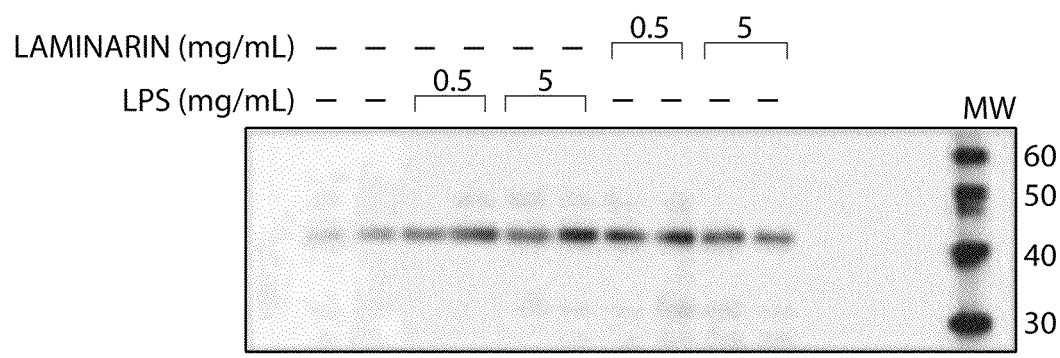
FIG. 4F shows the tGNBP-2 expression following exposure of termites to either LPS or laminarin at either 0.5 or 5 mg/mL (left/right lanes in each sample represent two independent repeats).
Figure 4G:
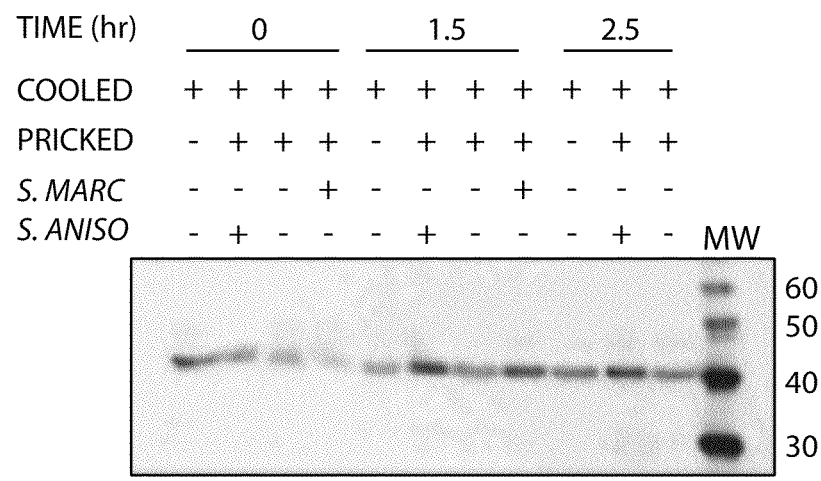
FIG. 4G shows the expression level of tGNBP-2 following termite infection with either *M. anisopliae* (*M. aniso*) or *S. marcescens* (*S. marc*). Cooled-only (Cooled) or cooled and pricked (Pricked) termites are shown as controls.

The presence of active tGNBP-2 in nest material indicates that termites incorporate but also maintain the levels of this protein in the nest structure. This observation points to a possible mechanism wherein tGNBP-2 functions as a nest-embedded sensor that cleaves and releases pathogenic components, which then prime termites for improved antimicrobial immunity. Indeed, termites exposed to either gram-negative bacteria-derived lipopolysaccharide (LPS) or an algae-derived $\beta(1,3)$-D-glucan, show improved resistance to *M. anisopliae* infection (FIG. 4E). Analysis of tGNBP-2 expression revealed significant upregulation following exposure to either molecular component (FIG. 4F). Induction of tGNBP-2 expression was also observed as early as 1.5 hours post-infection with either *Serratia marcescens* or *M. anisopliae*, in equivalence to *Drosophila* GNBP (20), while control groups for stress caused by cooling and pin-pricking remained close to baseline levels (FIG. 4G). This is in agreement with a report of *Drosophila* GNBP (20) and shows that tGNBP-2 is pattern-specific rather than stress induced. The use of tGNBP-2 as an external defense system is likely to have been instrumental in the evolution of complex societies with elaborate nest architectures. Moreover, evolution of social behaviors, like the increased mutual grooming observed following exposure to fungal pathogens (23), may have been directed by the protective function of salivary tGNBP-2.

tGNBP-2 is an Antimicrobial Effector Molecule

Figure 4H:
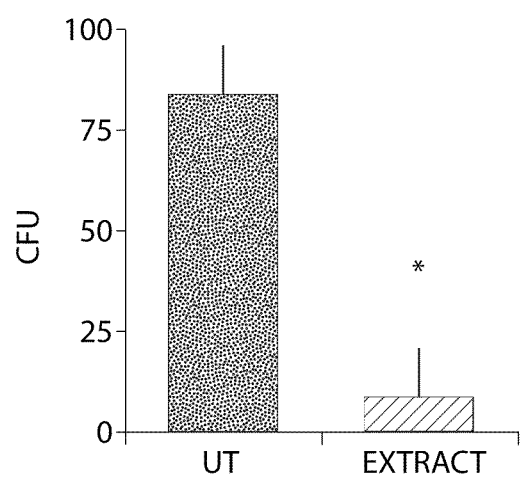
FIG. 4H demonstrates the effect of crude termite extract on conidial growth (in CFU) on potato-dextrose agar plates (*, $p<0.05$ vs. untreated conidia).
Figure 4I:
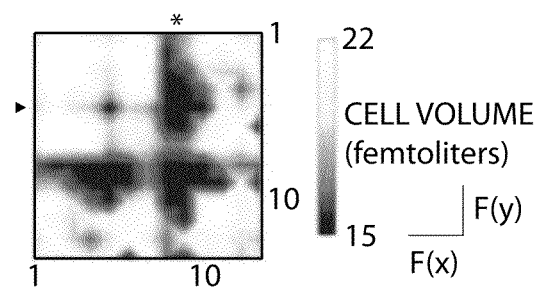
FIG. 4I provides a cytotoxicity map of fractionated termites on *M. anisopliae* conidia measured by cell volume in femtoliters. F(x),F(y) represent fractions 1-13 on either axis. tGNBP-2$^+$ fraction is marked by an arrowhead, antimicrobial peptide-containing fraction is marked by an asterisk.
Figure 4J:
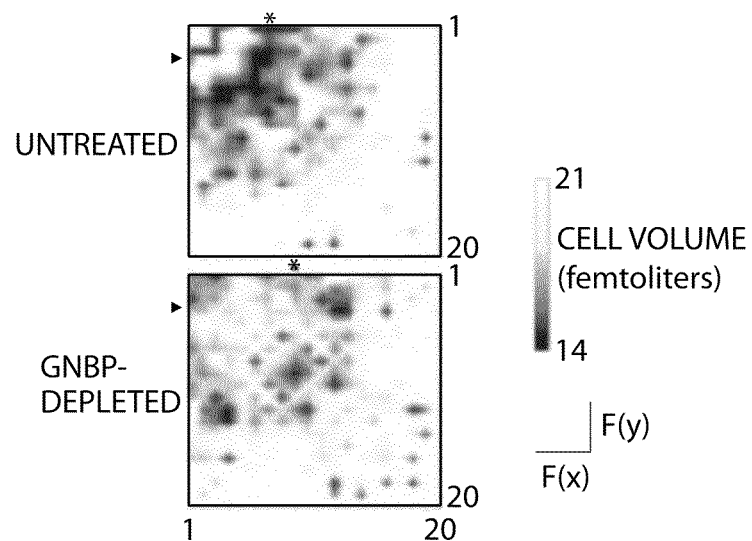
FIG. 4J demonstrates the loss of cytotoxicity following depletion of tGNBP-2 by antibody precipitation. F(x),F(y) represent fractions 1-20 on either axis.
Figure 4K:
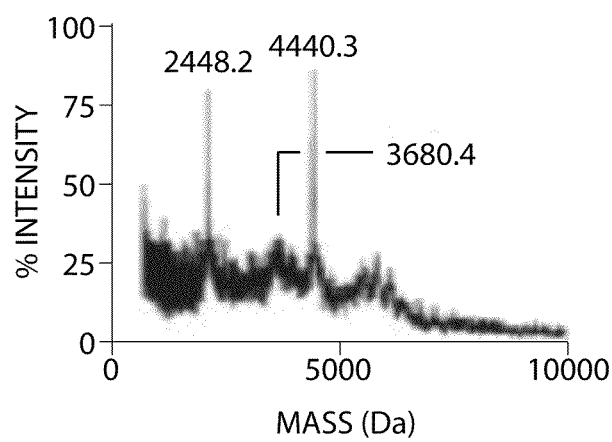
FIG. 4K provides results from a MALDI-MS analysis of the ~5 KDa termite fraction showing prominent peaks potentially coinciding with antimicrobial peptides, mass in Daltons.

Two important questions were (a) is the β(1,3)-glucanase activity of tGNBP-2 an effector activity, and (b) does this activity critically contribute to the total effector capacity of the termite immune system, or is it redundant to additional mechanisms? Crude termite extract, representing the total effector capacity, is cytotoxic to *Metarhizium* conidia (FIG. 4H). To observe this at higher resolution, the extract was fractionated into either 13 or 20 size fractions crossed in 13×13 or 20×20 matrices, respectively, and the cytotoxicity of every fraction combination towards *Metarhizium* was evaluated by flow cytometric analysis of conidia cell volume. Synergy between tGNBP-2 containing fractions and fractions of approximately 5 KDa molecules (FIG. 4I) was observed and resulted in significant synergistic cytotoxicity compared with that exerted by tGNBP-2 alone. This synergistic effect subsequently abolished by depletion of tGNBP-2 (FIG. 4J). Interestingly, tGNBP-2 appears to cooperate with antimicrobial peptides like termicin and spinigerin (24-26) possibly by compromising the cell wall integrity and enhancing peptide penetration into the cell, a mechanism employed by plant β(1,3)-glucanases (27). Strong evidence for these antimicrobial peptides was provided by peptide mass spectrometry (FIG. 4K). These antimicrobial peptides are constitutively expressed at high levels in termites, and mass spectrometric analysis suggested the presence of these peptides by size. Termicins are also secreted by salivary glands (26). Combinatorial cytotoxicity mapping demonstrates that tGNBP-2 is a critical component of the termite antimicrobial potential.

Structure/Function Analysis of the Pattern Recognition and Enzymatic Activity of tGNBP-2

Figure 5A:
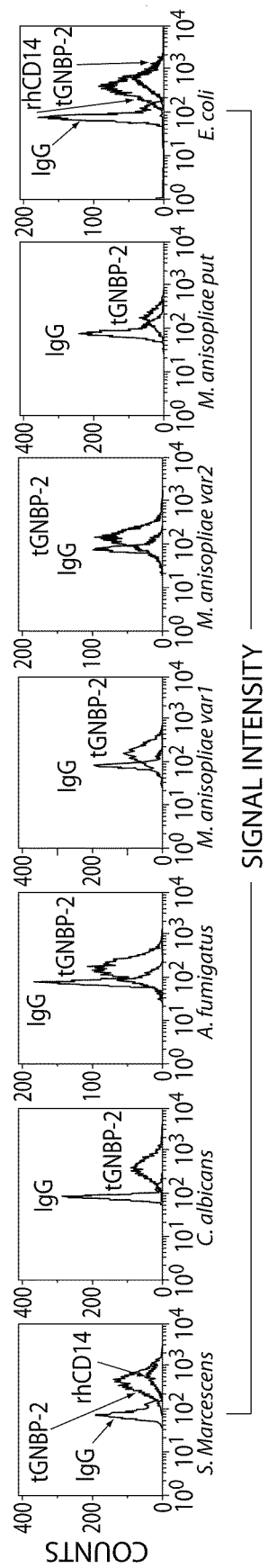
FIG. 5A illustrates the binding of tGNBP-2 to pathogenic bacteria and fungi (*Serratia marcescens, Candida albicans, Aspergillus fumigatus, Metarhizium anisopliae* variants 1 and 2, putative *M. anisopliae* isolated from a dead insect, *Escherichia coli*) compared with recombinant human CD14 (rhCD14). IgG=isotype controls, tGNBP-2=tGNBP-2 signal, rhCD14=recombinant human CD14 signal. LPS binding by tGNBP-2 does not interfere with its $\beta(1,3)$-glucanase activity, and laminarin does not interfere with fluorescent LPS binding. Isolated tGNBP-2 was exposed to increasing concentrations of LPS or GDL and its activity was measured by flow cytometry. Reciprocally, binding of fluorescent LPS to bead-linked tGNBP-2 was measured in the presence of laminarin or non-labeled LPS at increasing concentrations.

To examine whether tGNBP-2 represents a functional pattern recognition receptor, the interactions between this protein and a range of intact termite pathogens were quantified. Isolated tGNBP-2 exhibited binding to both gram-negative bacteria and fungi, with significantly higher affinity to bacteria than to fungi (FIG. 5A).

Figure 5B:
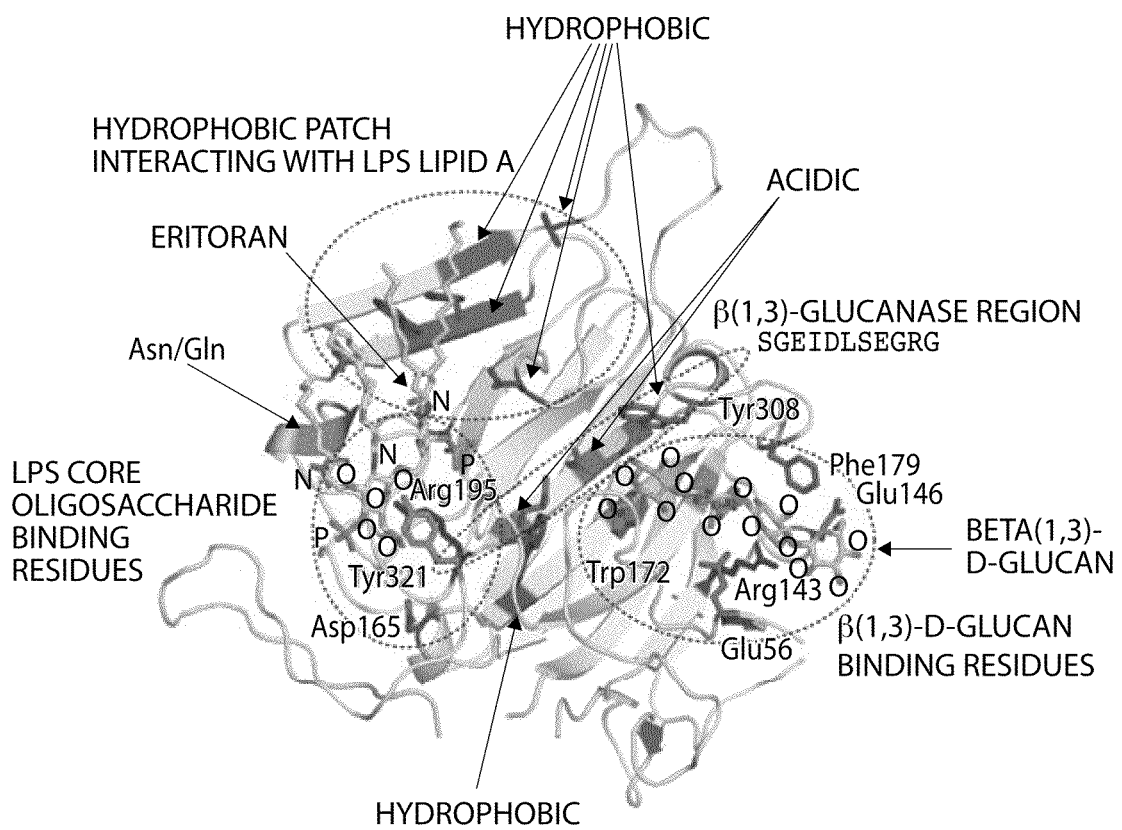
FIG. 5B provides a computational model of tGNBP-2 with side chains interacting with $\beta(1,3)$-D-glucan and eritoran (LPS analog) as follows: acidic, hydrophobic, basic, Asn/Gln, Tyr. $\beta(1,3)$-D-glucan C atoms are shown as well as eritoran C atoms, and O, P, and N for both.

To investigate the structural basis of this dual function, a homology based structural model of tGNBP-2 was constructed, and β(1,3)-D-glucan and eritoran (an LPS analog) were docked into it. This model suggests that β(1,3)-D-glucans are bound and catalyzed at the intact glucanase region, while a distinct hydrophobic patch upstream to it binds LPS (FIG. 5B). Homologous patches have been shown to bind LPS in other insects (28). The model also shows that the β(1,3)-D-glucan is held in place by 6 residues, 5 of which are chemically similar in termite GNBP-2 proteins and in *B. circulans* β(1,3)-glucanase, but vary among other insect GNBPs (Table 1), providing a structural insight into the enzymatic activity of tGNBP-2. Interestingly, it was found that binding of LPS and catalysis of β(1,3)-D-glucans do not cross-interfere with each other, showing that they are distinct both structurally and functionally.

TABLE 1

Comparison Between β(1,3)-glucan Binding Residues in GNBPs from Different Insects and *B. circulans*

| | β(1,3)-glucan binding residue | | | | | |
|---|---|---|---|---|---|---|
| | I | II | III | IV | V | VI |
| *N. graveolus* GNBP-2 | E | R | E | W | F | Y |
| *D. rubriceps* GNBP-2 | E | R | E | W | F | Y |
| *M. darwiniensis* GNBP-2 | E | R | E | W | Y | Y |
| *N. graveolus* GNBP-1 | E | R | D | W | E | Y |
| *D. rubriceps* GNBP-1 | E | R | D | W | E | Y |
| *M. darwiniensis* GNBP-1 | E | R | D | W | E | Y |
| *T. castaneum* GNBP | E | V | A | Y | P | Q |
| *D. melanogaster* GNBP-2 | D | H | N | M | Y | F |
| *D. melanogaster* GNBP-1 | D | S | E | L | W | Y |
| *B. mori* GNBP | E | T | I | L | K | Y |
| *H. cunea* GNBP | E | T | K | L | K | Y |
| *A. gambiae* GNBP-A | E | T | T | Y | F | Y |
| *A. gambiae* GNBP-B | D | R | S | W | A | H |
| *B. circulans* β(1,3)-glucanase | E | N | D | W | V | Y |

| Acidic |
|---|
| Hydrophobic |
| Basic |
| N/Q |
| Y |
| W |

Protein sequences were aligned with ClustalW and positions I-VI were extrapolated from computation model. Residue positions (in *N. graveolus* sequence) are: I 56, II 143, III 146, IV 172, V 179, VI 308.

Rational Design of a Glycomimetic Blocker of tGNBP-2

All these findings implicated the β(1,3)-glucanase activity of tGNBP-2 as an important receptor and effector molecule in termite antimicrobial defense. Therefore, a way to block this protein by targeting its unusual β(1,3)-glucanase activity and leave its other parts intact was sought. This requirement along with the aim of designing a pest control strategy highlighted a small molecule approach. It was thought that a glycomimetic derivative of the pathogenic patterns recognized by tGNBP-2 would be both a structurally rational and synthetically feasible blocker.

The combination of a pocket, formed by the 6 residues immobilizing the glycan, and the active core that flanks this pocket, determines that a β(1,3) glycosidic linkage can be the reducing-end determinant of the chain and presented to the active core. Therefore, a glucan chain (n≥1) with a terminal modification was hypothesized to occupy the receptor and hold it in an inactive state.

To validate this concept the simplest chain was started with—a single glucose molecule. Modification of the reducing end would provide a determinant probably sufficient to inactivate the receptor. It was found that glucose derivative D-δ-gluconolactone (GDL) completely satisfied these requirements. Structural analysis of tGNBP-2 showed that GDL could sufficiently occupy the active core of the receptor by making several contacts with the key glutamic acid residues in the active site (FIG. 5B).

Figure 5C:
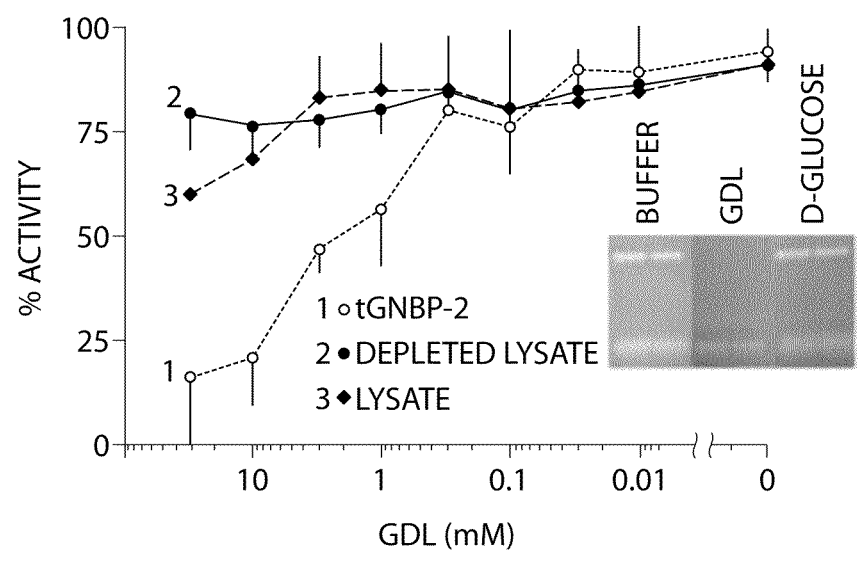
FIG. 5C shows the dose/response inhibition of $\beta(1,3)$-glucanase activity of tGNBP-2, termite lysate or tGNBP-2-depleted lysate by GDL. Inset shows zymogram of termite extract with GDL or D-glucose control.
Figure 5D:
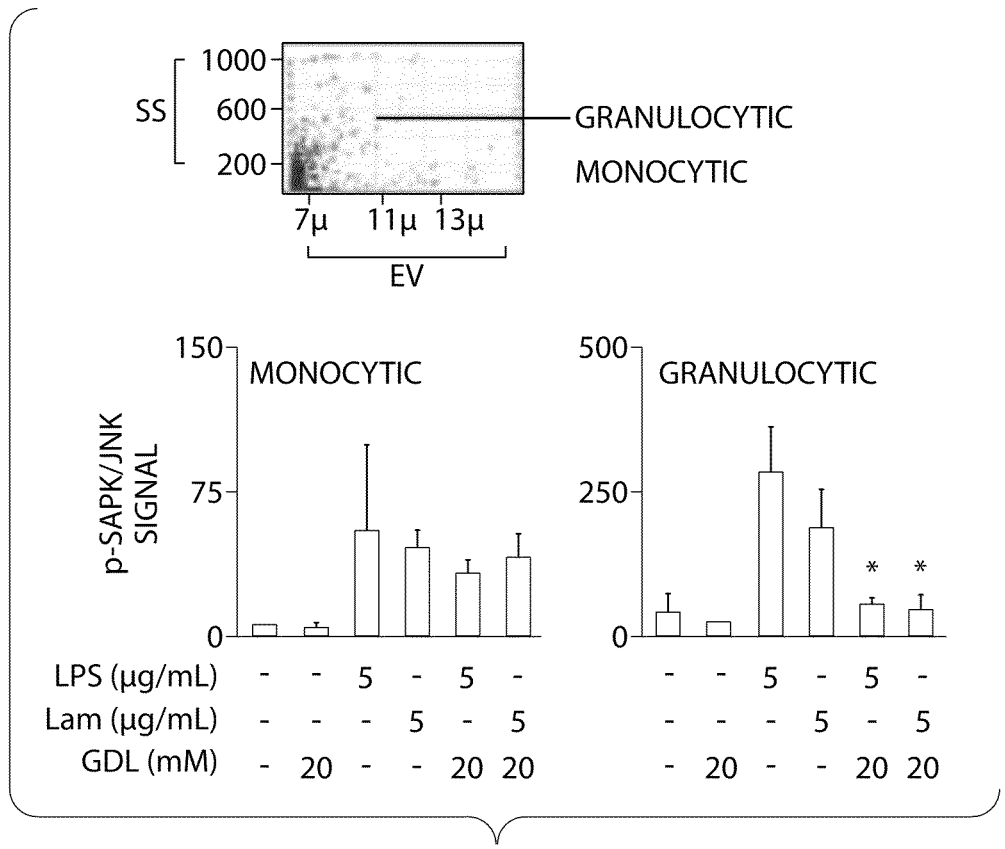
FIG. 5D demonstrates the inhibition of SAPK/JNK signaling in hemocytes by suppression of tGNBP-2 measured by flow cytometry (G, granulocytes; M, monocytes; GDL, D-δ-gluconolactone; n=2,000).
Figure 5E:
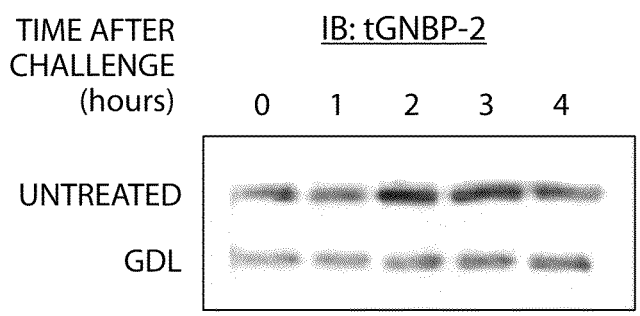
FIG. 5E shows that GDL (20 mM) blocks induction of tGNBP-2 by laminarin challenge on isolated termite cells, measured by Western blot.

GDL efficiently blocked the activity of tGNBP-2, but left other β-glucanases intact (FIG. 5C) indicating good specificity for the purpose of this study. In response to a β(1,3)-D-glucan challenge, termite hemocytes responded by SAPK/JNK phosphorylation (32). GDL inhibited this activation response, (FIG. 5D) and the subsequent induction of tGNBP-2 (FIG. 5E). Interestingly however, of the two hemocyte populations expressing tGNBP-2, GDL affected only the activation of granular hemocytes, suggesting that plasmatocytes have additional glucan-recognizing mechanisms and might have distinct roles in antimicrobial immunity.

GDL Suppresses Termite Antimicrobial Immunity In-Vivo

Figure 6A:
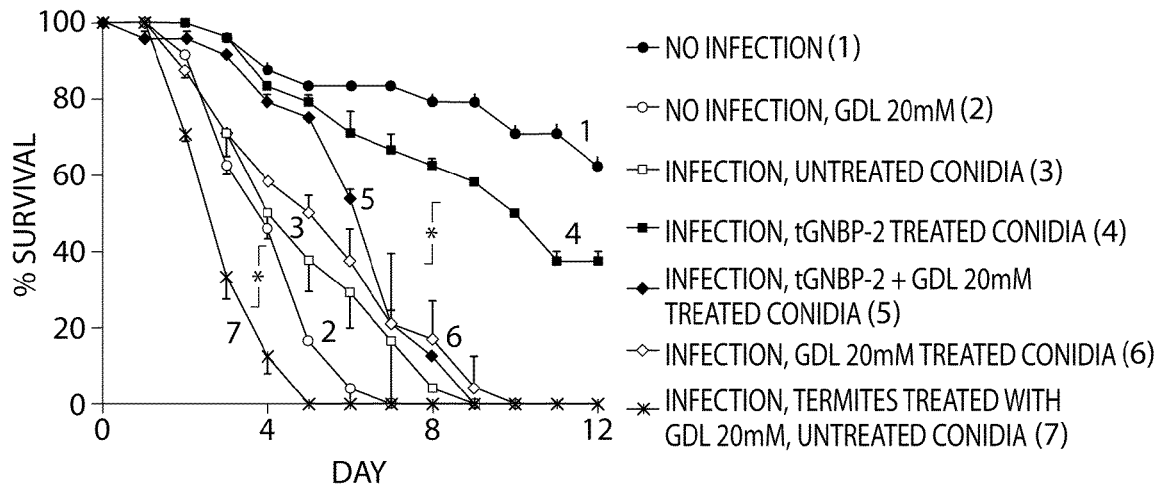
FIG. 6A demonstrates the effect of gain or loss of tGNBP-2 function on termites infected with *M. anisopliae* along the course of 12 days (GDL, D-δ-gluconolactone; mean of 2 groups, n=12/group; *, p<0.05 tGNBP-2 treated conidia vs. other groups, p<0.05 GDL treated termites with untreated conidia vs. other groups, n.s. no significant difference vs. no infection).
Figure 6B:
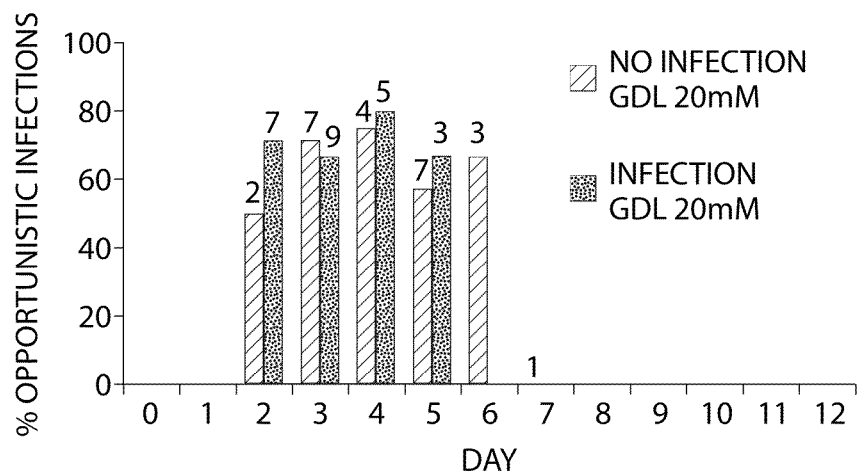
FIG. 6B shows results from a post-mortem analysis of dead termites from GDL treatment groups, representing % of termites confirmed to have been infected by microbial pathogens. Numbers above bars represent daily death count.
Figure 7:
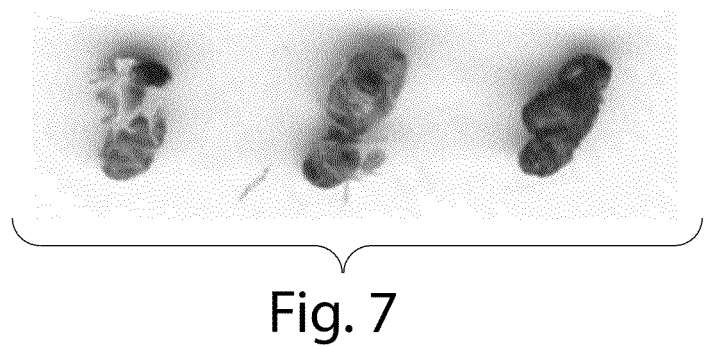
FIG. 7 illustrates the post-mortem analysis of infected termites. Dead termites were externally sterilized by 70% ethanol and incubated in sterile culture plates at RT for 4 days. Three representative termites are shown, the right termite showing characteristic signs of infection by *S. marcescens*.

Termites died rapidly following infection with *M. anisoplia*. When conidia were treated with isolated tGNBP-2 prior to the infection, termite survival was remarkably similar to that of uninfected groups, indicating that conidia were inactivated by tGNBP-2. However, GDL restored susceptibility to infection. On the other hand, termites treated with GDL for 24 hours prior to infection showed accelerated mortality (FIG. 6). GDL had no direct toxic effect on conidia themselves, as any inhibitory effect of fungal glucanases is likely irrelevant prior to germination. Interestingly, GDL treatment also caused accelerated mortality even in the absence of active infection. Post-mortem analysis pointed to pathogens other than *Metarhizium* in termite killing, suggesting that termites were killed by multiple opportunistic pathogens, namely gram negative bacteria, such as *Serratia* and *Pseudomonas*, and fungi, as well as by *M. anisopliae* (FIG. 7). Notably, these observations are unlikely to have resulted from inhibited feeding, because termite gut symbionts provide multiple pathways for polysaccharide utilization (33), many of which are not blocked by GDL (34). The different survival kinetics in the in vivo experiments are due to survivability variations among different *Nasutitermes* colonies used.

CONCLUSION

The strategy presented herein is a novel alternative to toxic pesticides given that it is natural, nontoxic, and biodegradable. GDL and similar glycomimetics could be engineered towards a field formulation with minimal adverse effects on surrounding ecosystems, for example, by using nanoparticles to immobilize them. Such nanoparticles have been demonstrated to be highly efficient in β(1,3)-glucanase inhibition in vitro. The strategy is believed to not be limited to termites, as the glucanase activity of tGNBP-2 appears to be shared by several pest species (16-18) as suggested by the sequence and structural analysis. In addition, since GDL is a product of a biosynthetic pathway, plants could be engineered to produce it in high amounts and at specific compartments, which would bolster their immunity to pest attacks. Glycomimetic synthesis in this context could be optimized so as to not interfere with future industrial utilization of plant carbohydrates as a non-fossil fuel source.

REFERENCES

1. Bischoff V, Vignal C, Boneca I G, Michel T, Hoffmann J A, & Royet J (2004) Nat Immunol 5, 1175-1180.
2. Janeway C A, Jr. & Medzhitov R (2002) Annu Rev b inninol 20, 197-216.
3. Lemaitre B, Nicolas E, Michaut L, Reichhart J M, & Hoffmann J A (1996) Cell 86, 973-983.
4. Dong Y, Taylor H E, & Dimopoulos G (2006) PLoS Biol 4, e229.
5. Watson F L, Puttmann-Holgado R, Thomas F, Lamar D L, Hughes M, Kondo M, Rebel V I, & Schmueker D (2005) Science 309, 1874-1878.
6. Bulmer M S & Crozier R H (2006) Mol Biol Evol 23, 317-326.
7. Jiggins F M & Kim K W (2006) J Mol Evol 63, 769-780.
8. Dimopoulos G, Richman A, Muller H M, & Kafatos F C (1997) Proc Natl Acad Sci USA 94, 11508-11513.
9. Keitel T, Simon O, Borriss R, & Heinemann U (1993) Proc Nall Acad Sci USA 90, 5287-5291.
10. Wan E, Das S, Dong Y, & Dimopoulos G (2008) Insect Mol Biol 17, 39-51.
11. Brown G D & Gordon S (2005) Cell Microbiol 7, 471-479.
12. Royet J & Dziarski R (2007) Nat Rev Microbiol 5, 264-277.
13. Planas A, Juncosa M, Lloberas J, & Querol E (1992) FEBS Lett 308, 141-145.
14. Miller L R (1997), pp. xi, 170 leaves.
15. Rosengaus R B, Moustakas J E, Calleri D V, & Traniello J F (2003) J Insect Sci 3, 31.
16. Balasubramani V, Sayyed A H, & Crickmore N (2008) J Econ Entomol 101, 1911-1918.
17. Genta F A, Terra W R, & Ferreira C (2003) Insect Biochem Mol Bio133, 1085-1097.
18. Pauchet Y, Freitak D, Heidel-Fischer H M, Heckel D G, & Vogel H (2008) J Biol Chem.
19. Lomer C J, Bateman R P, Johnson D L, Langewald J, & Thomas M (2001) Annu Rev Entomol 46, 667-702.
20. Kim Y S, Ryu J H, Han S J, Choi K H, Nam K B, Jang I H, Lemaitre B, Brey P T, & Lee W J (2000) J Biol Chem 275, 32721-32727.
21. Labeta M O, Landmann R, Obrecht J P, & Obrist R (1991) Mol Immunol 28, 115-122.
22. Metheniti A, Giannakas N, Katsoulas H L, Soldatos A N, Tsakas S, & Lambropoulou M (2003) Arch Insect Biochem Physiol 54, 25-36.
23. Traniello J F, Rosengaus R B, & Savoie K (2002) Proc Natl Acad Sci USA 99, 6838-6842.
24. Bulmer M S & Crozier R H (2004) Mol Biol Evol 21, 2256-2264.
25. Da Silva P, Jouvensal L, Lamberty M, Bulet P, Caille A, & Vovelle F (2003) Protein Sci 12, 438-446.
26. Lamberty M, Zachary D, Lanot R, Bordereau C, Robert A, Hoffmann J A, & Bulet P (2001) J Biol Chem 276, 4085-4092.
27. Park S W, Lawrence C B, Linden J C, & Vivanco J M (2002) Plant Physiol 130, 164-178.
28. Bilej M, De Baetselier P, Van Dijck E, Stijlemans B, Colige A, & Beschin A (2001) J Biol Chem 276, 45840-45847.
29. Cianciotto N, Rappuoli R, & Groman N (1986) JB acteriol 168, 103-108.
30. Copa-Patino J L, Reyes F, & Perez-Leblic M I (1989) FEMS Microbiol Lett 53, 285-291.
31. Pitson S M, Seviour R J, McDougall B M, Stone B A, & Sadek M (1996) Biochern J316 Pt 3), 841-846.
32. Sluss H K, Han Z, Barrett T, Goberdhan D C, Wilson C, Davis R J, & Ip Y T (1996) Genes Dev 10, 2745-2758.
33. Warnecke F, Luginbuhl P, Ivanova N, Ghassemian M, Richardson T H, Stege J T, Cayouette M, McHardy A C, Djordjevic G, Aboushadi N, et al. (2007) Nature 450, 560-565.
34. de A X F, de Paula Silveira F Q, & Filho E X (1996) Curr Microbiol 33, 71-77.
35. Higgins D G, Thompson J D, & Gibson T J (1996) Methods Enzymol 266, 383-402.

36. Wilgenbusch J C & Swofford D (2003) Curr Protoc Bioinformatics Chapter 6, Unit 64.
37. Rosengaus R B, Cornelisse T, Guschanski K, & Traniello J F (2007) Naturwissenschaften 94, 25-33.
38. Irish J M, Hovland R, Krutzik P O, Perez O D, Bruserud O, Gjertsen B T, & Nolan G P (2004) Cell 118, 217-228.
39. Kalix S & Buchenauer H (1995) Electrophoresis 16, 1016-1018.
40. Meunier F & Wilkinson K J (2002) Biomacromolecules 3, 857-864.
41. Hartshorn K L, White M R, & Crouch E C (2002) Infect Immun 70, 6129-6139.

Although the invention has been described in detail for the purpose of illustration, it is understood that such detail is solely for that purpose and variations can be made by those skilled in the art without departing from the spirit and scope of the invention which is defined by the following claims.

The contents of all references, patents and published patent applications cited throughout this application are incorporated herein by reference. The citation of any of the references, patents and published patent applications, however, is not intended to be an admission that the reference, patent or published application is prior art.

What is claimed is:

1. A method for providing protection against or treating a pest infestation consisting of:
   contacting a pest, soil, wood, plant, seeds, grain or manmade structure with a carbohydrate-based inhibitor that inhibits $\beta(1,3)$-glucanase activity of gram-negative bacteria binding protein (GNBP) in an amount effective to protect against or to treat the pest infestation,
   wherein the carbohydrate-based inhibitor does not inhibit cellulase or stimulate feeding in the pests of the pest infestation.

2. The method of claim 1, wherein the carbohydrate-based inhibitor does not inhibit $\alpha$ and/or $\beta$-1,4-glucosidase in the pests of the pest infestation.

3. The method of claim 1, wherein carbohydrate-based inhibitor inhibits $\beta(1,3)$-glucanase activity and not the activity of another glucanase and/or glucosidase in the pests of the pest infestation.

4. The method of claim 1, wherein the carbohydrate-based inhibitor is not gluconolactone.

5. The method of claim 1, wherein the carbohydrate-based inhibitor comprises a $\beta(1,3)$ glycosidic linkage at a reducing end.

6. The method of claim 1, wherein the carbohydrate-based inhibitor is conjugated to a nanoparticle.

7. The method of claim 1, wherein the carbohydrate-based inhibitor is conjugated to a dendrimer.

8. The method of claim 1, wherein the carbohydrate-based inhibitor is conjugated to polyacrylamide.

9. The method of claim 1, wherein the carbohydrate-based inhibitor is a di/tri/tetrameric $\beta(1,3)$-D-glucan derivative or a di/tri/tetrameric $\beta(1,3)$-L-glucan derivative.

10. The method of claim 9, wherein the di/tri/tetrameric $\beta(1,3)$-D-glucan derivative or di/tri/tetrameric $\beta(1,3)$-L-glucan derivative is D-Glc-$\beta(1,3)$-D-glucono-$\Delta$-lactone, D-Glc-$\beta(1,3)$-D-Glc-$\beta(1,3)$-D-Glc-$\beta(1,3)$-D-glucono-$\Delta$-lactone, L-Glc-$\beta(1,3)$-L-glucono-$\Delta$-lactone or L-Glc-$\beta(1,3)$-L-Glc-$\beta$(1,3)-L-Glc-$\beta(1,3)$-L-glucono-$\Delta$-lactone.

11. The method of claim 1, wherein the carbohydrate-based inhibitor is a $\beta(1,3)$-D-glucan-LPS (lipopolysaccharide) conjugate or a $\beta(1,3)$-L-glucan-LPS conjugate.

12. The method of claim 11, wherein the $\beta(1,3)$-D-glucan-LPS conjugate is eritoran-D-glucono-$\Delta$-lactone.

13. The method of claim 11, wherein the $\beta(1,3)$-L-glucan-LPS conjugate is eritoran-L-glucono-$\Delta$-lactone.

14. The method of claim 11, wherein the $\beta(1,3)$-D-glucan or $\beta(1,3)$-L-glucan is conjugated to the LPS with an acyl spacer.

15. The method of claim 11, wherein the $\beta(1,3)$-D-glucan or $\beta(1,3)$-L-glucan is conjugated to the LPS with a heterobifunctional cross-linker.

16. The method of claim 1, wherein the carbohydrate-based inhibitor is a polyvalent D-glucono-D-lactone-LPS conjugate or a polyvalent L-glucono-L-lactone-LPS conjugate.

17. The method of claim 16, wherein the polyvalent D-glucono-D-lactone-LPS conjugate or a polyvalent L-glucono-L-lactone-LPS conjugate is conjugated to a nanoparticle.

18. The method of claim 16, wherein the polyvalent D-glucono-D-lactone-LPS conjugate or a polyvalent L-glucono-L-lactone-LPS conjugate is conjugated to a dendrimer.

19. The method of claim 16, wherein the polyvalent D-glucono-D-lactone-LPS conjugate or a polyvalent L-glucono-L-lactone-LPS conjugate is conjugated to polyacrylamide.

20. The method of claim 16, wherein the polyvalent D-glucono-D-lactone or polyvalent L-glucono-L-lactone is D-$\delta$-gluconolactone (GDL).

21. The method of claim 16, wherein the LPS is eritoran.

22. The method of claim 1, wherein the GNBP is GNBP-1 or GNBP-2.

23. The method of claim 22, wherein the GNBP is GNBP-2.

24. The method of claim 1, wherein the pest infestation is an insect infestation.

25. The method of claim 1, wherein the pest infestation is a plant pest infestation.

26. The method of claim 1, wherein the pest infestation is a/an termite, fly, moth, ant, beetle, mosquito, silk worm, locust or cockroach infestation.

27. The method of claim 26, wherein the pest infestation is a termite infestation.

28. The method of claim 27, wherein the termites of the termite infestation are of the *N. corniger, Z. augusticollis, C. secundus, R. virginicus* or *R. flavipes* species.

29. The method of claim 1, wherein the contacting comprises applying or spraying the carbohydrate-based inhibitor onto the pest, soil, wood, plant, seeds, grain or manmade structure.

30. The method of claim 1, wherein the contacting comprises soaking the pest, soil, wood, plant, seeds, grain or manmade structure with the carbohydrate-based inhibitor.

31. The method of claim 1, wherein the contacting comprises incorporating or impregnating the carbohydrate-based inhibitor into the pest, soil, wood, plant, seeds, grain or manmade structure.

32. The method of claim 1, wherein the method further comprises contacting the pest, soil, wood, plant, seeds, grain or manmade structure with another pesticide.

33. The method of claim 32, wherein the other pesticide is an insecticide, fungicide or a herbicide.

34. The method of claim 1, wherein the carbohydrate-based inhibitor is in an aqueous composition.

35. The method of claim 1, wherein the carbohydrate-based inhibitor is in a dry formulation.

* * * * *